(12) United States Patent
Chen et al.

(10) Patent No.: US 9,037,214 B2
(45) Date of Patent: May 19, 2015

(54) MULTI-MODALITY NANOPARTICLES HAVING OPTICALLY RESPONSIVE SHAPE

(75) Inventors: Fanqing Chen, Moraga, CA (US); Louis-Serge Bouchard, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 454 days.

(21) Appl. No.: 13/202,976

(22) PCT Filed: Feb. 23, 2010

(86) PCT No.: PCT/US2010/025097
§ 371 (c)(1),
(2), (4) Date: Feb. 6, 2012

(87) PCT Pub. No.: WO2010/096828
PCT Pub. Date: Aug. 26, 2010

(65) Prior Publication Data
US 2012/0136241 A1    May 31, 2012

Related U.S. Application Data

(60) Provisional application No. 61/154,721, filed on Feb. 23, 2009.

(51) Int. Cl.
| | |
|---|---|
| B82Y 15/00 | (2011.01) |
| A61K 49/00 | (2006.01) |
| A61K 49/18 | (2006.01) |
| A61K 49/22 | (2006.01) |
| B22F 1/00 | (2006.01) |
| B22F 1/02 | (2006.01) |
| B82Y 30/00 | (2011.01) |
| A61K 51/12 | (2006.01) |
| B82Y 5/00 | (2011.01) |

(52) U.S. Cl.
CPC ....... *A61K 49/0002* (2013.01); *Y10T 428/2991* (2013.01); *A61K 49/183* (2013.01); *A61K 49/1857* (2013.01); *A61K 49/1866* (2013.01); *A61K 49/1875* (2013.01); *A61K 49/225* (2013.01); *B22F 1/0018* (2013.01); *B22F 1/025* (2013.01); *B82Y 5/00* (2013.01); *B82Y 30/00* (2013.01); *A61K 51/1244* (2013.01); *B22F 2998/00* (2013.01); *Y10S 977/902* (2013.01); *Y10S 977/89* (2013.01); *Y10S 977/888* (2013.01); *Y10S 977/712* (2013.01)

(58) Field of Classification Search
CPC ... A61K 49/183; A61K 49/0065; B82Y 15/00
USPC ............... 424/9.1, 9.322, 9.42, 646; 428/403, 428/570; 427/412; 977/712, 888, 890, 902, 977/904
See application file for complete search history.

(56) References Cited

U.S. PATENT DOCUMENTS

| | | | |
|---|---|---|---|
| 6,828,786 B2 | 12/2004 | Scherer et al. | |
| 7,829,140 B1 * | 11/2010 | Zhong et al. | .............. 427/212 |
| 2004/0209376 A1 | 10/2004 | Natan et al. | |
| 2005/0025969 A1 * | 2/2005 | Berning et al. | .............. 428/403 |
| 2005/0059031 A1 | 3/2005 | Bruchez et al. | |
| 2006/0148104 A1 | 7/2006 | Marini et al. | |
| 2006/0204794 A1 | 9/2006 | Kikuchi et al. | |
| 2006/0249705 A1 | 11/2006 | Wang et al. | |
| 2008/0112886 A1 | 5/2008 | Mitragotri et al. | |
| 2009/0004248 A1 | 1/2009 | Bunick et al. | |

OTHER PUBLICATIONS

Sung-Jin et al. Gold-coated iron nanoparticles: a novel magnetic resonance agent for T1 and T2 weighted imaging, Nanotechnolgy, 17, 640-644, 2006.*
Min-Chen et al. Gold-coated iron nanoparticles for biomedical applications, Journal of Applied Physics, 93, 7551-7553, 2003.*
Wei-Wu et al. Magnetic Iron Oxide Nanoparticles: Synthesis and Surface Functionalization Strategies, Nanoscale Res. Lett, 2008, 3, 397-415.*
International Search Report and Written Opinion for International Application No. PCT/US10/25097 mailed Apr. 28, 2010.
Mulder WJ et al., FASEB J. Dec. 2005;19(14):2008-10.
Saikat Mandal and Kannan M. Krishnan, J. Mater. Chem., 2007,17, 372-376.
T. Bala et al., J. Mater. Chem., 2004,14, 1057-1061.

* cited by examiner

*Primary Examiner* — Jake Vu
*Assistant Examiner* — Jagadishwar Samala
(74) *Attorney, Agent, or Firm* — Tom Hunter; Weaver Austin Villeneuve & Sampson LLP

(57) ABSTRACT

In certain embodiments novel nanoparticles (nanowontons) are provided that are suitable for multimodal imaging and/or therapy. In one embodiment, the nanoparticles include a first biocompatible (e.g., gold) layer, an inner core layer (e.g., a non-biocompatible material), and a biocompatible (e.g., gold) layer. The first gold layer includes a concave surface that forms a first outer surface of the layered nanoparticle. The second gold layer includes a convex surface that forms a second outer surface of the layered nanoparticle. The first and second gold layers encapsulate the inner core material layer. Methods of fabricating such nanoparticles are also provided.

18 Claims, 13 Drawing Sheets

MULTI-MODALITY NANOPARTICLES HAVING OPTICALLY RESPONSIVE SHAPE

RELATED APPLICATIONS

This application is the national phase application of International application number PCT/US2010/025097, filed Feb. 23, 2010, which claims priority to and the benefit of U.S. Provisional Application No. 61/154,721, filed on Feb. 23, 2009, which is hereby incorporated by reference in its entirety.

STATEMENT OF GOVERNMENTAL SUPPORT

This invention was made with government support under Contract No. DE-AC02-05CH11231 awarded by the U.S. Department of Energy. The government has certain rights in the invention.

FIELD OF THE INVENTION

The present invention relates to the field of nanoparticles and, more particularly, to the field of examination of living tissue where nanoparticles are used to enhance such examination.

BACKGROUND OF THE INVENTION

In MRI, magnetic materials such as gadolinium chelates and magnetic nanoparticles are often employed to enhance image contrast (see, e.g., Lu et al. (2006) *Nanotechnology* 17: 5812-5820, which is referred to herein as, "Lu, J., et al.") The magnetic nanoparticles are passivated by biocompatible coatings such as dextrin, citrate, polystyrene/divinylbenzene and elemental gold. These coatings also detoxify the particles, resulting in enhanced lifetimes in vivo. Typical examples of magnetic nanoparticulate core-shell configurations include magnetite-dextrin, magnetite-silica (see, e.g., Lu et al. (2007) *Nano Letts.*, 7: 149-154) and iron-gold (see, e.g., Cho et al. (2006) *Nanotechnology* 17: 640-644).

Laser-based photoacoustic tomography (PAT) (see, e.g., Wang et al. (2003) *Nat. Biotechnol,* 21: 803-806) is a hybrid imaging modality. It uses a pulsed laser source to illuminate a biological sample. Light absorption by the tissue results in a transient temperature rise on the order of approximately 10 mK. The rapid thermoelastic expansion excites ultrasonic waves that are measured using broadband ultrasonic transducers conformally arranged around the sample. Finally, a modified back-projection reconstruction algorithm is used to construct a map of the distribution of the optical energy deposition within the sample. The spatial resolution of PAT is not limited by optical diffusion, but instead by the bandwidth of the acoustic detectors. It has been shown that PAT can depict subsurface tissue structures and functional changes noninvasively with a resolution better than 100 µm. Like other optical modalities, PAT is highly sensitive in mapping and quantifying the dynamic distribution of optical contrast agents such as metallic nanocolloids and organic dyes.

Dual modality nanoparticles for MRI and another imaging modality have been developed by others (see, e.g., Mulder et al. (2005) *FASEB J.,* 19: 2008-2010; and Prinzen et al. (2007) *Nano Letters* 7: 93-100) None of these dual modality nanoparticles address the dual modalities of MRI and PAT.

SUMMARY OF THE INVENTION

In various embodiments, this invention pertains to nanoparticles useful for multimodal imaging and/or therapy, methods of making such nanoparticles, and methods of using such nanoparticles. In certain embodiments, the nanoparticles are nanowontons useful for MRI and PAT imaging.

In various embodiments, this invention pertains to nanoparticles useful for multimodal imaging and/or therapy, methods of making such nanoparticles, and methods of using such nanoparticles. In certain embodiments, the nanoparticles are nanowontons useful for MRI and PAT imaging.

In certain embodiments a layered nanoparticle is provided comprising a first biocompatible layer having a substantially concave surface that forms a first outer surface of the layered nanoparticle; an inner core material layer; and a second biocompatible layer having a substantially convex surface that forms a second outer surface of the layered nanoparticle, the first and second layers encapsulating the core material layer. In certain embodiments the inner core material comprises a material selected from the group consisting of a magnetic material (e.g., a ferro-magnetic material, a paramagnetic material, a superparamagnetic material, etc.), a radioactive material, a pharmaceutical, a toxin, etc. In certain embodiments the inner core material comprises a non-biocompatible material (e.g., a material that when contacted with a biological tissue and/or fluid reacts with the tissue and/or fluid and/or is toxic to an organism). In certain embodiments the inner core material comprises a material selected from the group consisting of cobalt Co, iron (Fe), nickel (Ni), and platinum (Pt), or an alloy thereof, a nitrate nitrite, or nitride thereof, or an oxide thereof. In certain embodiments the inner core material comprises a ferro-magnetic material (e.g., a material selected from the group consisting of iron (Fe), nickel (Ni), cobalt (Co) and gadolinium (Gd), or an alloy thereof, a nitrate, nitrite, or nitride thereof, or an oxide or hypoxide thereof or a sulfate, sulfite thereof). In certain embodiments the inncer core material comprises a radioactive material (e.g., $^{125}$I, $^{35}$S, $^{14}$C, $^{32}$P, $^{11}$C, $^{38}$K, $^{89}$Zr, $^{217}$Bi, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{90}$Y, $^{131}$I, $^{123}$I, $^{99}$In, $^{64}$Cu, $^{68}$Ga, and $^{111}$Ag, and the like). In certain embodiments the first biocompatible layer and/or the second biocompatible layer independently comprise a material selected from the group consisting of gold, aluminum, titanium, niobium, tantalum, nickel, ruthenium, rhodium, palladium, silver, osmium, iridium, platinum, nitenol, and a cobalt base alloy, or an alloy thereof, a nitrate nitrite, or nitride thereof, or an oxide or hypoxide thereof. In certain embodiments the first biocompatible layer and the second biocompatible layer comprise the same material. In certain embodiments the first biocompatible layer and the second biocompatible layer comprise different materials. In certain embodiments the nanoparticle absorbs radiation over a range selected from the group consisting of infrared wavelength visible light wavelength, ultraviolet wavelength, microwave wavelength, and x-ray wavelengths. In certain embodiments the first biocompatible layer comprises gold; the inner core material comprises cobalt; and the second biocompatible layer comprises gold.

In various embodiments the longest dimension of the nanoparticle is less than or equal to about 500 nm, or less than or equal to about 400 nm, or less than or equal to about 300 nm, or less than or equal to about 200 nm, or less than or equal to about 100 nm, or less than or equal to about 80 nm, or less than or equal to about 60 nm, or less than or equal to about 50 nm, or less than or equal to about 40 nm, or less than or equal to about 30 nm, or less than or equal to about 25 nm, or less than or equal to about 20 nm. In certain embodiments the first biocompatible layer ranges in thickness from about 1 nm, about 2 nm, about 5 nm, or about 10 nm to about 100 nm, about 50 nm, about 30 nm, about 20 nm, or about 10 nm; the inner core material ranges in thickness from about 1, about 2 nm, about 5 nm, about 10 nm, or about 20 nm to about 100 nm, about 80 nm, about 60 nm, or about 40 nm and the second biocompatible layer ranges in thickness from about 1 nm, about 2 nm, about 5 nm, or about 10 nm to about 100 nm, about 50 nm, about 30 nm, about 20 nm, or about 10 nm. In certain embodiments the nanoparticle is attached to second moiety (e.g., a protein, an antibody, and a nucleic acid, a lectin, etc.).

Methods are also provided for examining a cell, organ, or tissue. The methods typically involve introducing nanoparticles (e.g., nanowontons) described and/or claimed herein into the tissue; and detecting at least some of the nanoparticles by a first modality selected from the group consisting of MRI, PAT, PET, ESR, x-ray, CAT, ultrasound, single photon emission computed tomography (SPECT), thermography, electrical impedance tomography, and optical coherence tomography to produce detection data. In certain embodiments the method further involves detecting at least some of the nanoparticle by a modality different than the first modality. In certain embodiments the first modality is nuclear magnetic resonance, thereby producing nuclear magnetic resonance data. In certain embodiments the method further comprises forming a magnetic resonance image from the nuclear magnetic resonance data. In certain embodiments the administering is by a route selected from the group consisting of parenteral administration, oral administration, rectal administration, inhalation, intravenous administration, intruder u| administration, subdermal administration. In certain embodiments the nanoparticles are introduced to the tissue at concentration between about 1 pM and 10 nM, In certain embodiments the method further comprises detecting at least a portion of the nanoparticles by a modality other than nuclear magnetic resonance (e.g., via a method such as PAT, PET, ESR, x-ray, CAT, ultrasound, single photon emission computed tomography (SPECT), thermography, electrical impedance tomography, optical coherence tomography, and the like). In certain embodiments the second modality comprises photoacoustic tomography thereby producing photoacoustic tomography data. In certain embodiments the method further comprises forming an image from the nuclear magnetic resonance data and the photoacoustic tomography data. In certain embodiments the examining comprises in vivo imaging of a living human or non-human mammal (e.g., primate, equine, poricine, canine, feline, largomorph, etc.).

Also provided is the use of the layered nanoparticles described and/or claimed herein in the manufacture of a multi-modal imaging reagent. In certain embodiments the imaging reagent is formulated for administration to a mammal via a route selected from the group consisting of parenteral administration, oral administration, rectal administration, inhalation, intravenous administration, intrarterial administration, subdermal administration. In certain embodiments the nanoparticles are designed for detection by two or more modalities selected from the group consisting of MRI, PAT, PET, ESR, x-ray, CAT, ultrasound, single photon emission computed tomography (SPECT), thermography, electrical impedance tomography, and optical coherence tomography). In certain embodiments the imaging reagent is formulated at a nanoparticle concentration ranging from about 1 pM to about 10 nM, In certain embodiments the composition of the nanoparticles is suitable for detection by a modality other than nuclear magnetic resonance. In certain embodiments the modality other than MRI comprises a method selected from the group consisting of PAT, PET, ESR, x-ray, CAT, ultrasound, single photon emission computed tomography (SPECT), thermography, electrical impedance tomography, optical coherence tomography.

Methods are also provided for making a layered nanoparticle (e.g., a nanowonton). The methods typically involve providing a substrate comprising a plurality of features, each feature providing a convex surface raised above the substrate; depositing layers on the convex surface to form a nanoparticle, the layers in order comprising a first biocompatible layer; an inner core material layer; and a second biocompatible layer; and performing an etch that separates the nanoparticle from the convex surface. In certain embodiments the method further comprises depositing a sacrificial layer (e.g., chromium) on the convex surface before depositing the first biocompatible layer. In certain embodiments the features are selected from the group consisting of a nanopillar, a nanosphere, a nanowire, and a nanotube. In certain embodiments the providing a substrate comprising a plurality of features comprises forming the features on a substrate; and forming a substantially convex surface on a top of the features. In certain embodiments the feature comprises a nanopillar. In certain embodiments the forming the feature comprises forming an array of the features; and forming a substantially convex surface on the top of the feature comprises forming the substantially convex surface of the top of at least a plurality of the features; depositing the layers on the convex surface comprises depositing the layers on the convex surface of at least a plurality of the features, thereby forming the precursor of a plurality of nanoparticles; and performing the sacrificial etch separates the nanoparticles from the nanopillars. In certain embodiments forming the feature comprises forming a silicon feature on a silicon substrate. In certain embodiments the feature is a poly-silicon feature. In certain embodiments the feature and/or the substrate is a single crystal silicon feature and/or substrate. In certain embodiments forming the substantially convex surface on the top of the feature comprises forming a silicon oxide nanostructure having a substantially convex shape on the top of the feature. In certain embodiments forming the silicon oxide nanostructure on the top of the feature comprises heating the silicon feature in an oxygen environment. In certain embodiments the method further comprises annealing the features. In certain embodiments depositing the sacrificial layer comprises depositing the sacrificial layer material at an angle with respect to an axis of the feature(s) while rotating the substrate, the sacrificial material layer forming the substantially convex surface. In certain embodiments performing an etch comprises placing the substrate in a basic solution (e.g., KOH) that dissolves at least a portion of the substrate to release the nanoparticles. In certain embodiments the method further comprises separating the nanoparticles from the basic solution. In various embodiments the inner core material comprises a material selected from the group consisting of a magnetic material (e.g., a ferro-magnetic material, a paramagnetic material, a superparamagnetic material, etc.) a radioactive material, a pharmaceutical, and a toxin. In certain embodiments the inner core material comprises a non-biocompatible material. In certain embodiments the inner core material comprises a material selected from the group consisting of cobalt Co, iron (Fe), nickel (Ni), and platinum (Pt), or an alloy thereof, a nitrate nitrite, or nitride thereof, or an oxide thereof. In certain embodiments the inner core material comprises a ferro-magnetic material comprising a material selected from the group consisting of iron (Fe), nickel (Ni), cobalt (Co) and gadolinium (Gd), or an alloy thereof, a nitrate nitrite, or nitride thereof, or an oxide thereof. In certain embodiments the inner core material comprises a radioactive material (e.g., $^{125}$I, $^{35}$S, $^{14}$C, $^{32}$P, $^{11}$C, $^{38}$K, $^{89}$Zr, $^{217}$Bi, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{98}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{90}$Y, $^{131}$I, $^{123}$I, $^{99}$In, $^{131}$I, $^{64}$Cu, $^{68}$Ga, and $^{111}$Ag, and the like). In certain embodiments the first biocompatible layer and/or the second biocompatible layer comprises a material selected from the group consisting of gold, aluminum, titanium, niobium, tantalum, nickel, ruthenium, rhodium, palladium, silver, osmium, iridium, platinum, nitenol, and a cobalt base alloy, or an alloy thereof, a nitrate nitrite, or nitride thereof or an oxide or hypoxide thereof. In certain embodiments the first biocompatible layer and the second biocompatible layer comprises the same material. In certain embodiments the first biocompatible layer and the second biocompatible layer comprise different materials. In certain embodiments the inner core material comprises cobalt; the first biocompatible layer comprises gold; and the second biocompatible layer comprises gold.

In certain embodiments of the method, the longest dimension of the nanoparticle is less than or equal to about 500 nm, or less than or equal to about 400 nm, or less than or equal to about 300 nm, or less than or equal to about 200 nm, or less than or equal to about 100 nm, or less than or equal to about 80 nm, or less than or equal to about 60 nm, or less than or equal to about 50 nm, or less than or equal to about 40 nm, or less than or equal to about 30 nm, or less than or equal to about 25 nm, or less than or equal to about 20 nm. In certain embodiments of the method the first biocompatible layer ranges in thickness from about 1 nm, about 2 nm, about 5 nm, or about 10 nm to about 100 nm, about 50 nm, about 30 nm, about 20 nm, or about 10 nm; the inner core material ranges in thickness from about 1, about 2 nm, about 5 nm, about 10 nm, or about 20 nm to about 100 nm, about 80 nm, about 60 nm, or about 40 nm and the second biocompatible layer ranges in thickness from about 1 nm, about 2 nm, about 5 nm; or about 10 nm to about 100 nm, about 50 nm, about 30 nm, about 20 nm, or about 10 nm. In certain embodiments the nanoparticle is attached to second moiety (e.g., a protein, an antibody, and a nucleic acid, a lectin, etc.).

Also provided are kits comprising a container containing nanoparticles as described and/or claimed herein and instructional materials teaching the use of the nanoparticles as imaging reagents.

DEFINITIONS

The term "nanoparticle" refers to a particle having a submicron (µm) size. In various embodiments, microparticles have a characteristic size (e.g., diameter) less than about 1 µm, 800 nm, or 500 nm, preferably less than about 400 nm, 300 nm, or 200 nm, more preferably about 100 nm or less, about 50 nm or less or about 30 or 20 nm or less.

The term "biocompatible" when used with reference to a biocompatible material indicates that the material elicits little o/no immune response in a given organism, or is able to integrate with a particular cell type or tissue or is stable and substantially chemically inert when in the body of an organism.

The term "cancer marker" refers to a biomolecule such as a protein that is useful in the diagnosis and/or prognosis of cancer. As used herein, "cancer markers" include but are not limited to: PSA, human chorionic gonadotropin, alpha-fetoprotein, carcinoembryonic antigen, cancer antigen (CA) 125, CA 15-3, CD20, CDH13, CD 31, CD34, CD105, CD146, D16S422HER-2, phospatidylinositol 3-kinase (PI 3-kinase), trypsin, trypsin-1 complexed with alpha(1)-antitrypsin, estrogen receptor, progesterone receptor, c-erbB-2, bc1-2, S-phase fraction (SPF), p185erbB-2, low-affinity insulin like growth factor-binding protein, urinary tissue factor, vascular endothelial growth factor, epidermal growth factor, epidermal growth factor receptor, apoptosis proteins (p53, Ki67), factor VIII, adhesion proteins (CD-44, sialyl-TN, blood group A, bacterial lacZ, human placental alkaline phosphatase (ALP), alpha-difluoromethylornithine (DFMO), thymidine phosphorylase (dTHdPase), thrombomodulin, laminin receptor, fibronectin, anticyclins, anticyclin A, B, or E, proliferation associated nuclear antigen, lectin UEA-1, cea, 16, and von Willebrand's factor.

The terms "ligand" or "binding moiety", as used herein, refers generally to a molecule that binds to a particular target molecule and forms a bound complex. The binding can be highly specific binding, however, in certain embodiments, the binding of an individual ligand to the target molecule can be with relatively low affinity and/or specificity. The ligand and its corresponding target molecule form a specific binding pair. Examples include, but are not limited to small organic molecules, sugars, lectins, nucleic acids, proteins, antibodies, cytokines, receptor proteins, growth factors, nucleic acid binding proteins and the like which specifically bind desired target molecules, target collections of molecules, target receptors, target cells, and the like.

The terms "nucleic acid" or "oligonucleotide" refer to at least two nucleotides covalently linked together. A nucleic acid can be single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321 , O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Y. S. Sanghui and P. Dan Cook. Nucleic acids containing one or more carbocyclic sugars are also included within the definition of nucleic acids (see Jenkins et al. (1995), *Chem. Soc. Rev. pp* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage scFv, Fv, Fab and disulfide Fv (Reiter et al. (1995) *Protein Eng.* 8: 1323-4331).

The term "specifically binds", as used herein, when referring to a targeting ligand (e.g., protein, nucleic acid, antibody, etc.), refers to a binding reaction that is determinative of the presence of the target of the targeting ligand in a heterogeneous population of molecules (e.g., proteins and other biologics). Thus, under designated conditions (e.g. binding assay conditions), the specified ligand or preferentially binds to its particular "target" molecule and preferentially does not bind in a significant amount to other molecules present in the sample.

BRIEF DESCRIPTION OF THE DRAWINGS

FIG. 2A: Scanning electron microscopy image of nanowontons. FIG. 2B: Transmission electron microscopy image of three nanowontons in various diameters; notice that the lighter regions in the nanoparticle are relatively hollow, and are responsible for photothermal tuning properties of the nanowonton (Liu et al. (2006) *Nat. Mater.*, 5: 27-32). FIG. 2C: Particle diameter distribution of 150 nanowontons. Because of the inhomogeneous polysilicon nanopillar diameter, the size of the nanowontons varies from 30 to 90 nm, and the average diameter is 60 nm. FIG. 2D: Absorption spectrum of nanowonton, medium peak wavelength is ~700 nm. FIG. 2E: Spin-spin relaxation time $T_2$ measured at 20 MHz proton frequency and 37° C. $T_2$ begins to change when the concentration exceeds 20 pM. Note that although 20 MHz is much less than 300 MHz (used for the MRI), this gives a lower bound on relaxivity and shows that the contrast works even at low fields, such as those from portable NMR devices.

FIG. 3A: PAT image of 4 absorbing objects containing nanowonton contrast agent embedded in a gel phantom (5% agarose). The concentrations of nanowontons were 100, 50, 25, and 13 pM, respectively, for objects A, B, C, and D. FIG. 3B: Intensity profiles extracted from the image along four lines (horizontal and vertical dashed lines indicated on the image) going through the absorbing centers are plotted to highlight the visibility of nanowonton inclusions in the reconstructed image. With a CNR close to 1, the object D, where the nanowonton concentration is 13 pM, can hardly be recognized from the background, showing that the current PAT system has detection sensitivity on the order of 25 pM.

FIGS. 4A and 4B: Spin-echo images for the phantoms 4A and 4B, respectively, with an echo time (TE) of 50 ms and recycle time (TR) of 1 s. The higher-concentration samples appear darker in the images, with doped water used as a control and exhibiting the strongest $T_2$-weighted intensity. The concentrations of the gels are given in the figure along with the $T_2$ values that are deduced from a 7-point curve-fitting procedure. The field of view for this image is 3×3 cm, the number of points is 256×128, and the slice thickness is 1 mm. FIGS. 4C and 4D: Intensity profiles for the images in 4A and 4B. The relative intensities along a circular contour drawn through the middle of the gels are plotted as a function of the gel azimuthal angle from the x axis. The nanoparticles contrast remains detectable down to 2.5 pM. The images for phantom 4A and 4B are plotted to different (normalized) scales.

DETAILED DESCRIPTION

In various embodiments nanoparticles suitable as imaging reagents an multi-modal imaging reagents are provided. In addition methods of manufacturing the nanoparticles and methods of examining tissue(s) using such nanoparticle are also provided.

In various embodiments the nanoparticle imaging reagent(s) described herein can be readily detected using two or more different modalities. Such modalities include, for example two or more modalities selected from the group consisting of magnetic resonance imaging (MRI), photoacoustic tomography (PAT), x-ray imaging, ultrasonic imaging, and positron emission tomography (PET). In certain embodiments the particles are readily detected using MRI and PAT imaging.

In an embodiment of the method of examining living tissue, multimodality imaging may be employed. The multimodality imaging is based on complementary detection principles that have broad clinical applications and are believed to improve the accuracy of medical diagnosis. This means that a tracer particle (i.e. a nanoparticle as described herein) advantageously can incorporate multiple functionalities into a single vehicle.

In various embodiments the nanoparticle(s) described herein resemble the shape of a wonton and incorporate multiple layers comprising different materials. The "nanowonton" shape allows a single probe to incorporate and facilitate the complementary strategies of contrast-based volume imaging and edge detection. Inclusion of an inner core in biocompatible outer layers allows the use of otherwise toxic and/or reactive species for the inner core that are not otherwise useful in living organisms. Thus for example, by using strong ferromagnetic materials (e.g., ferromagnetic cobalt or iron) as the core, nanoparticles having a much larger magnetic dipole moment than materials conventionally used as MRI contrast agents (e.g., gadolinium, iron oxide) can be provided. Use of an inert outer material such as gold or platinum or protects the inner core and provides a substrate suitable for attachment e.g., using thiol chemistry or other linkers, of antibodies, oligonucleotides, peptides, or other small molecules or drugs. In addition, in various embodiments, the nanowontons described herein can be physically oriented by a magnetic field so a new relaxation time can be created beside of $T_1$ and $T_2$ to increase imaging contrast.

Nanowonton Nanoparticles.

Figure 11A:
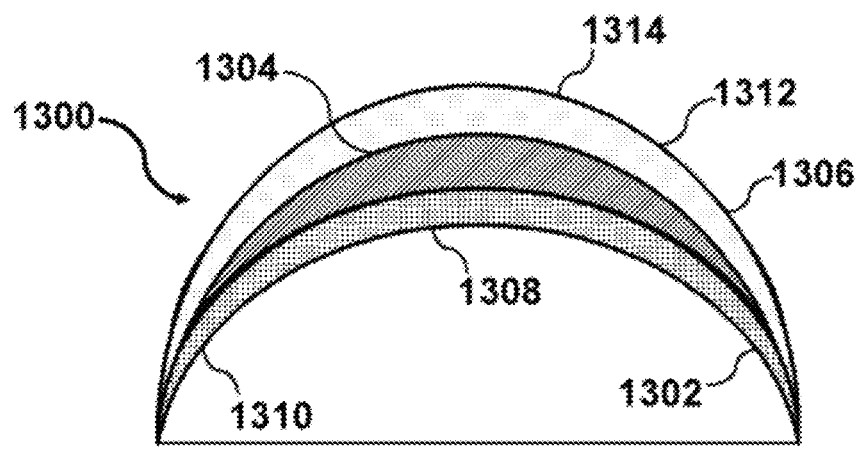
FIGS. 11A and 11B illustrate embodiments of nanowonton nanoparticles.
Figure 11B:
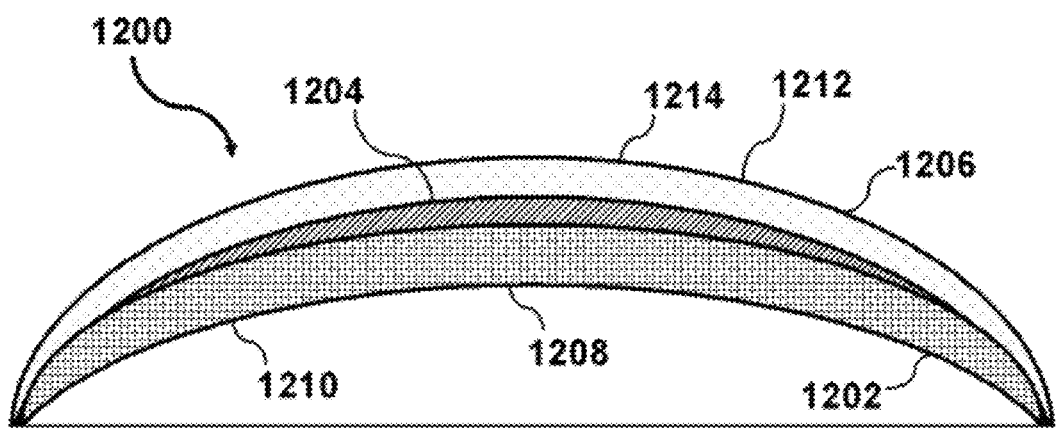

An illustrative embodiment of a nanowonton (wonton-shaped nanoparticle) is schematically illustrated in cross-section in FIG. 11B. The nanoparticle 1200 includes a first biocompatible (e.g., gold, platinum, etc.) layer 1202, a core material layer 1204 (which can be reactive and/or non-biocompatible), and a second biocompatible 1206 layer. The first biocompatible layer 1202 has a substantially concave surface 1208 that forms a first outer surface 1210 of the nanoparticle 1200. The second biocompatible layer 1206 has a substantially convex surface 1212 that forms a second outer surface 1214. The first and second gold layers, 1202 and 1206, encapsulate the inner core layer(s). In various embodiments the inner core layer(s) can include a magnetic material (e.g., a ferromagnetic material, a paramagnetic material, a superparamagnetic material), a radioactive material, a toxic (e.g., cytotoxic) material, a therapeutic material (e.g., a pharmaceutical), and the like. In certain embodiments the biocompatible layers can be fabricated by a material that degrades under certain conditions (e.g., acid, microwave, laser application, etc.) to release the inner core material at a particular time and/or location.

As used herein, a concave surface refers to a surface having a semi-spherical like surface with a radius of curvature that extends in a direction away from the center of the nanoparticle and that has a center for the radius of curvature that may vary. For example, a concave surface may be a surface that is rounded inward like the inside of a bowl. A substantially concave surface means that some portion or portions of the surface need not be concave.

As used herein, a convex surface means a surface having a semi-spherical like surface with a radius of curvature that extends in a direction towards or around the center of the nanoparticle, that may extend past a concave surface of the nanoparticle, and that has a center for the radius of curvature that may vary. For example, a convex surface may be rounded outward like a portion of a sphere. A substantially convex surface means that some portion or portions of the surface need not be convex.

Another illustrative embodiment of a nanoparticle of the present invention is illustrated in a cross-sectional view in Figure 11A. This differs from the nanoparticle illustrated in FIG. 11B principally in particle size and radius of curvature of the surface(s). The nanoparticle 1300 includes a first biocompatible (e.g., gold, platinum, etc.) layer 1302, one or more inner core layers 1304 (e.g., non-bio-compatible material layer(s), and a second biocompatible 1306 layer. The first biocompatible layer 1302 has a substantially concave surface 1308 that forms a first outer surface 1310 of the nanoparticle 1300. The second biocompatible layer 1306 has a substantially convex surface 1312 that forms a second outer surface 1314. The first and second gold layers, 1302 and 1306, encapsulate the inner core material layer(s) 1304.

It will be appreciated that where single biocompatible layer(s) and inner core layers are illustrated in FIGS. 11A and 11B, one or more of these layers can themselves comprise multiple layers each, for example, having different composition/chemical properties.

Biocompatible Layers

The biocompatible layers (top and bottom) comprising the nanoparticles can comprise any of a number of useful materials. In various embodiments the biocompatible layers comprise one or more noble metals and/or alloys, oxides, hypoxides, nitrides, nitrates, nitrites, and/or sulfides, sulfites, or sulfates thereof. Illustrative suitable materials include, but are not limited to the noble metals (e.g., ruthenium, rhodium, palladium, silver, osmium, iridium, platinum, gold) and/or mixtures or alloys thereof. Other suitable biocompatible materials include, but are not limited to titanium and titanium alloys, aluminum and aluminum alloys, chromium and chromium alloys, cobalt base alloys (e.g., as MP35N, elgiloy, ASTM-F75, ASTM-F90, satellite, etc.), nickel and nickel alloys (e.g., nitinol), and the like. In various embodiments oxides, hypoxides, nitrates, nitrides, nitrites, sulfates, and sulfites of the various metals, and metal alloys are contemplated.

In certain embodiments, the biocompatible layers include one or more non-metallic materials. Such non-metallic materials include, but are not limited to silica/glass, ceramics, certain minerals (e.g., quartz), biocompatible polymers (e.g., PEEK® polymers (polyaryletherketones), MOTIS® polymers (carbon fiber/PEEK composites), co-polymers of silicone and/or polyurethane), and the like.

Inner Core Materials

In various embodiments the internal core layers can include biocompatible materials or, by virtue of the outer layers that are biocompatible, materials that are not biocompatible. Illustrative inner core layer materials include, but are not limited to magnetic materials, radioactive materials, materials suitable for electron spin resonance detection and/or heating, cytotoxic materials, polymeric materials, and/or pharmaceuticals.

In certain embodiments, the inner core material(s) comprise a magnetic material (e.g., a ferromagnetic material, a paramagenetic material, a superparamagnetic material, etc.) and/or a magnetic alloy. Suitable magnetic materials include, but are not limited to magnetic materials selected from the group consisting of Al, Co, Mn, Nd, Fe, Ni, Gd, B, Sm, and Mo, mixtures thereof, alloys thereof, nitrites, nitrates, or nitrides thereof, sulfites or sulfates /thereof, oxides or hypoxides thereof, and the like. In certain embodiments suitable magnetic materials include materials such as $MM'_2O_4$, and $M_xO_y$, where each M or M' independently represents Co, Fe, Ni, Mn, Zn, Gd, or Cr, and $0<x<=3$, and $0<y<=5$). In certain embodiments the magnetic alloy comprises an alloy selected from the group consisting of CoCu, CoPt, FePt, CoSm, NiFe and NiFeCo.

In certain embodiments the inner core materials comprise one or more radioactive materials. Such radioactive materials can be used for radiotherapy and/or for various detecting methods (e.g., positron emission tomography). Suitable core materials include, but are not limited to one or more materials selected from the group consisting of $^{125}$I, $^{35}$S, $^{14}$C, $^{32}$P, $^{11}$C, $^{38}$K, $^{89}$Zr, $^{217}$Bi, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{142}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{90}$Y, $^{131}$I, $^{123}$I, $^{99}$In, $^{131}$I, $^{64}$Cu, $^{68}$Ga, $^{211}$At, and $^{111}$Ag.

In certain embodiments the inner core layer materials comprise a material suitable for electron spin resonance imaging and/or heating. Such materials are well known to those of skill in the art (see, e.g., U.S. Patent Publication No: US 2005/0118102 A1. In various embodiments the Material is a superparamagnetic material with an electron spin resonance (ESR) Q greater than 10, greater than 100 or greater than 1000. Illustrative materials comprise a garnet or a spinel, a yttrium ion garnet (YIG), a yttrium ion garnet substituted with a material such as aluminum, gallium, indium, ferrite, and the like.

In certain embodiments the inner core layer material comprises a cytotoxin and/or a drug. Illustrative cytotoxins and/or drugs include, but are not limited to drugs used to treat cancer (e.g., alkylating agents such as busulfan, chlorambucal, cisplatinum, cyanomorpholinodoxorubicin, etc., antimitotic agents such as allocolchicine, cohchicine, taxol, vinblastine, vincristine, and the like, topoisomerase I inhibitors such as camptothecin, aminocamptothecin, and the like, topoisomerase II inhibitors such as doxorubicin, amonafide, daunorubicin, deoxydoxorubicin, mitoxantrone, and the like, RNA/DNA antimetabolites such as acivicin, ftorafur, methotrexate, trimetrexate, and the like; DNA antimetabolites such as 2'deoxy-5-fluorouridine, cyclocytidine, guanazolk, and the like).

Such inner core layer materials are illustrative and not limiting. Using the teachings provided herein, other useful inner core materials will be recognized by one of skill in the art.

Dimensions.

In various embodiments the nanoparticles (nanowontons) described herein, range in size from about 5 nm up to about 1000 nm (longest dimension). In certain embodiments the longest dimension of the nanoparticle is less than or equal to about 500 nm, or less than or equal to about 400 nm, or less than or equal to about 300 nm, or less than or equal to about 200 nm, or less than or equal to about 100 nm, or less than or equal to about 80 nm, or less than or equal to about 60 nm, or less than or equal to about 50 nm, or less than or equal to about 40 nm, or less than or equal to about 30 nm, or less than or equal to about 25 nm, or less than or equal to about 20 nm. In certain embodiments the nanoparticle ranges from about 2 nm, 5 nm, 10 nm, 15 nm, or 20 nm up to about 500 nm, 400 nm, 300 nm, 200 nm, 100 nm, 60 nm, 50 nm, 40 nm, or about 30 nm. In certain embodiments the nanoparticle ranges from about 2 nm, 5 nm, or 15 nm up to about 100 nm, 90 nm, 80 nm, 70 nm, 60 nm, or 50 nm. In certain embodiments the nanoparticle has a mean maximum length of about 60 nm.

In various embodiments the first biocompatible layer and/or the second biocompatible layer ranges in maximum thickness from about 1 nm up to about 100 nm or about 50 nm, or from about 2 nm up to about 40 nm, or from about 5 nm up to about 30 nm, or from about 10 nm up to about 20 nm.

In various embodiments the inner core layer ranges in maximum thickness from about 1 nm up to about 100 nm or about 50 nm, or from about 2 nm up to about 40 nm, or from about 5 nm up to about 30 nm or 20 nm, or from about 10 nm up to about 20 nm.

In various embodiments the size, shape and materials selected for the nanoparticles are chosen so the nanoparticles absorb energy in the visible light spectrum (about 30 nm to about 750 nm) and/or in the infrared spectrum, and/or in the ultraviolet spectrum, and/or in the radio spectrum, and/or in the microwave spectrum, and/or in the terahertz spectrum, and/or in the x-ray spectrum.

In certain embodiments the size, shape and materials selected for the nanoparticles are chosen so the nanoparticles heat in response to the application of electromagnetic or optical radiation and therefore are useful for various hyperthermic treatment modalities. In certain embodiments the nanoparticles are designed to undergo spin resonance heating (e.g., heating as a consequence of magnetic resonance, nuclear magnetic resonance, electron spin resonance, etc.).

In certain embodiments the biocompatible outer layer(s) are designed to degraded under certain chemical and/or physical conditions to release the inner core material(s) at particular locations and/or at particular times. Thus, for example, in certain embodiments, the biocompatible outer layer(s) are designed to degrade in response to laser microwave radiation, in response to x-ray irradiation, at certain pH, and the like.

In various embodiments the size, shape and materials selected for the nanoparticles are chosen so the are detectable by two or more modalities. For example, the nanoparticles can be designed to be detectable by two or more modalities selected from the group consisting of MRI, PAT, PET, ESR, x-ray, CAT, ultrasound, single photon emission computed tomography (SPECT), thermography, electrical impedance tomography, optical coherence tomography and the like.

Illustrative Nanowonton.

By way of illustration, the fabrication and use of nanowonton nanoparticles described herein is detailed in Example 1. The nanoparticles described therein were synthesized for dual-modality MRI and photoacoustic tomography (PAT). The incorporation of MRI and PAT into a single probe offered the unique possibility of combining the complementary strategies of contrast-based volume imaging and edge detection. The nanoparticles illustrated in Example 1 include zero valence ferromagnetic cobalt (Co) particles with a gold (Au) coating for biocompatibility, and a unique "wonton" shape rendering increased optical absorption over a broad range of frequencies.

These nanowonton particles are well suited for use in diagnostic radiology and targeted molecular imaging. Such nanoparticulate contrast agents, with the desirable imaging (and other) properties of high chemical specificity, biocompatibility and a reasonable half-life, can be administered to a cell, a tissue, an organ, and/or an organism. In nanoparticle-based imaging studies, higher particle concentrations lead to better signal-to-noise ratios, but have hereto for posed a trade-off with the toxicity. The nanoparticles provide a good signal at extremely low nanoparticle concentrations.

The nanmowontons in Example 1 were characterized by scanning and transmission electron microscopy, absorption spectroscopy and NMR retaxometry (FIG. 2). The nanowontons exhibited a combination of ferromagnetic and optical responses making them well suited for dual-modality MRI and PAT studies. Measurements of NMR $T_2$ retaxivity reveal a per-particle retaxivity $1\times10^7$ $s^{-1}nM^{-1}$ (see, e.g., Table 2).

Previously, the oxidation-induced instability and toxicity of Co nanoparticles have prohibited their wide use as MRI contrast agents, but in the present case, the Au coating circumvented this issue. Furthermore, the shape and thickness of the Au capping layer was designed so that the center of its optical absorption range matches the NIR laser excitation wavelength used in PAT imaging (~700 nm) optimizing the photothermal response. Similar geometry-dependent optical absorption for nanostructures such as nanocrescents has been shown (see, Lu et al. (2005) *Nano Letters* 5: 119-124) and the nanowontons described herein provide similar wavelength tunabaity for PAT and other detection methods.

The highly stable, thin film (10 nm in the nanowontons illustrated in Example 1) gold (Au) coating provides a high level of biocompatibility. Furthermore, the biocompatible layer deposition process can be well controlled to allow tunable absorption spectra, allowing PAT at different optical wavelengths (see Example 1, Supporting Information and FIG. 7), A variety of gold nanocolloids are already entering in vivo clinical trials (see, e.g., Wang, et al. (2004) *Nano Letts.*, 4: 1689-1692). Among them, Au nanorods present particularly good optical absorption in the near-infrared region, tunable by changing the aspect ratio. It has already been demonstrated that gold nanorod contrast agents can be imaged with PAT, both ex vivo and in vivo. (see, e.g., Chamberland et al. (2008) *Nanotechnology* 19: 95-101; and Eghtedari et al. (2007) *Nano Lett* 7: 1914-1918.) Our study has shown that the sensitivity of PAT in imaging the nanowonton is equivalent to that for gold nanorods. In fact, the MRI contrast is also expected to be strongly dependent on the shape of the nanoconstruct. It is envisaged that nanorods or needle-shaped structures can elicit greater contrast because of larger shape-induced susceptibility gradients. The present nanowonton shape is, to first order, a compromise between optical and magnetic responses. Furthermore, the Au sandwich structure also allows additional tuning of absorbed wavelengths (see, Lu et a (2006) *Nat. Nanotechnol.*, 1: 47-52; PCT Application No: PCT/US2007/020026; Liu et a (2007) *J. Nanosci. Nanotechnol.*, 7: 2323-2330.) This can further improve the sensitivity of the PAT technique. The Au coatings are also especially attractive because of the possibility of conjugating the particles with specific molecules such as antibodies, specific ligands, thiol functional groups and therapeutic drugs, opening up prospects for targeted molecular imaging (see, e.g., Wickline et al. (2002) *J. Cell Bioehem.*, 39: 90-97). An additional imaging modality built into our nanoconstruct is the optical thermal conversion capability making these structures highly suited for photothermal therapy (see, e.g., Liu et al. (2006) *Nature Materials* 5: 27-32).

Nanowonton Fabrication.

Figure 1:
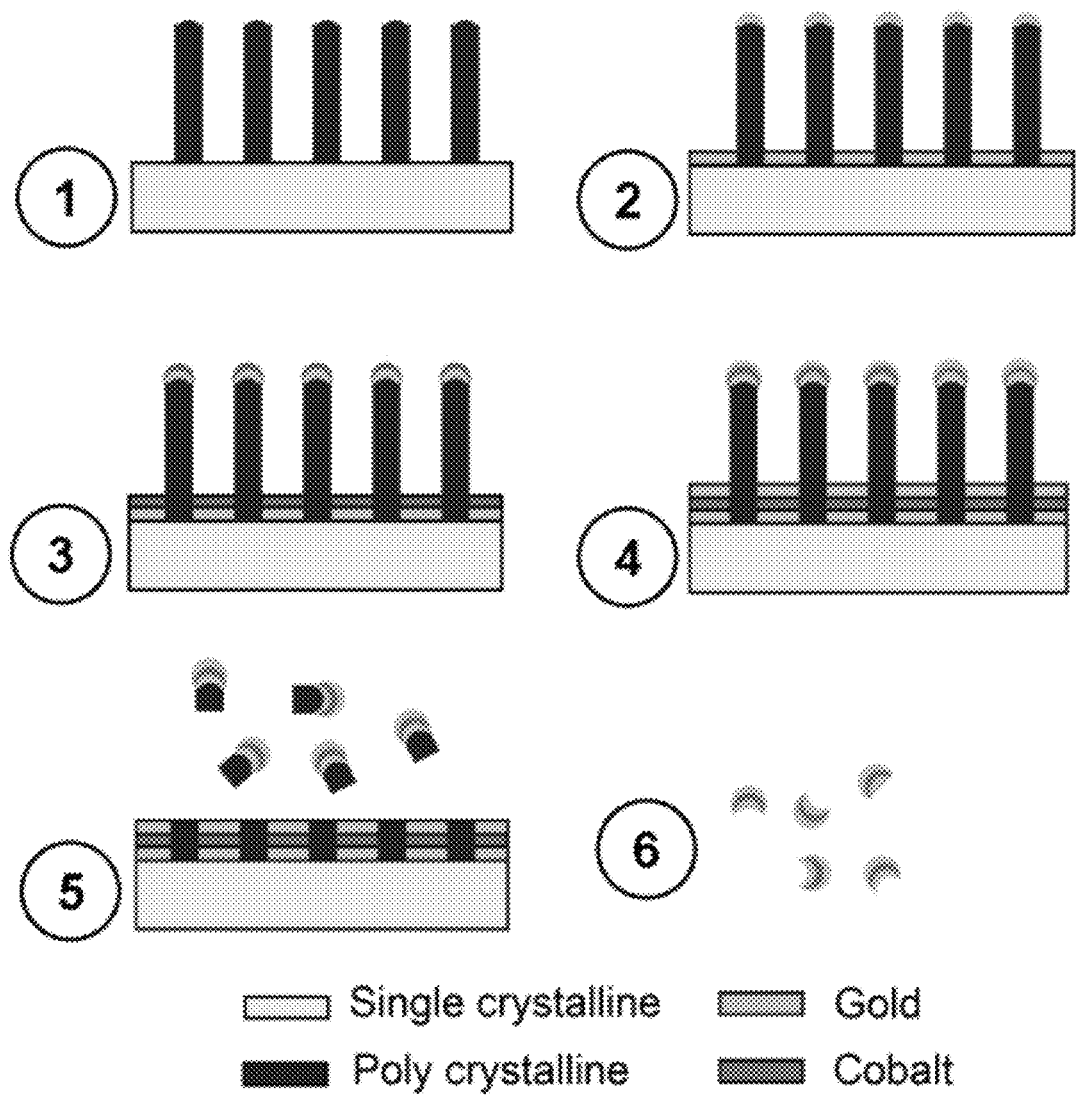
FIG. 1 illustrates a fabrication procedure for nanowontons, Six steps are illustrated: (1) Etching polysilicon nanopillars on the surface of single crystalline silicon wafer (for simpler presentation, we omitted from the illustration the preparatory step of depositing 5 nm of chromium before going to step 2, see Methods); (2) deposition of a 10-nm gold thin film; (3) deposition of 10-nm cobalt thin film; (4) deposition of 10-nm gold thin film; (5) etching polysilicon nanopillars in KOH batch solution; and (6) complete removal of polysilicon and chromium by KOH etching and separation of nanowontons.
Figure 2A:
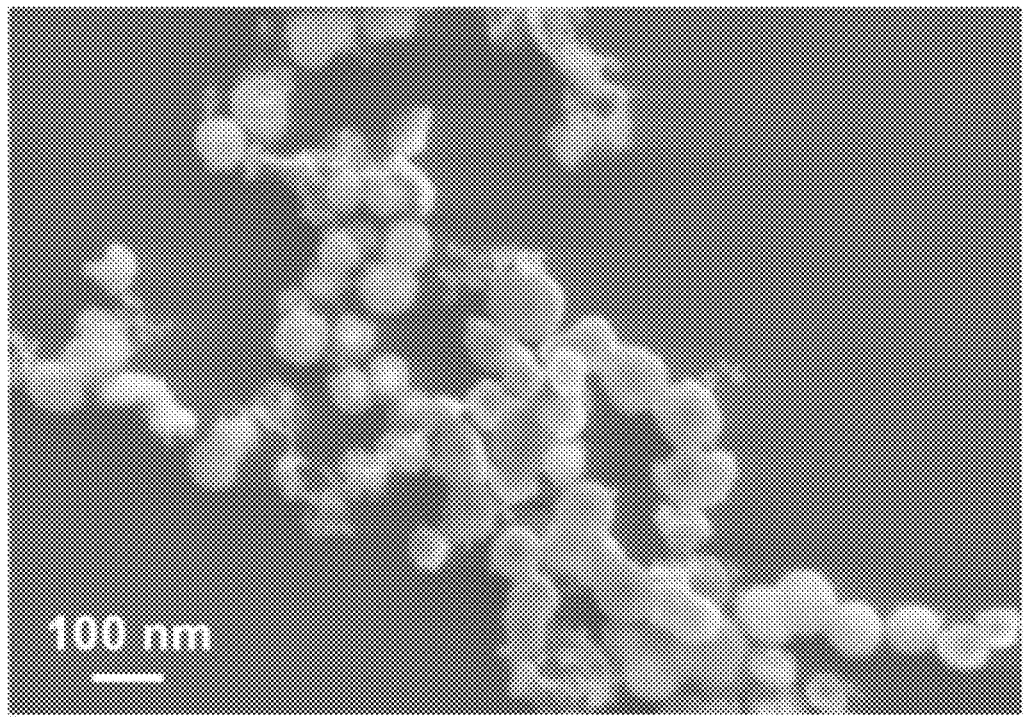
FIGS. 2A-2E show the characterization of illustrative cobalt nanowontons.
Figure 2B:
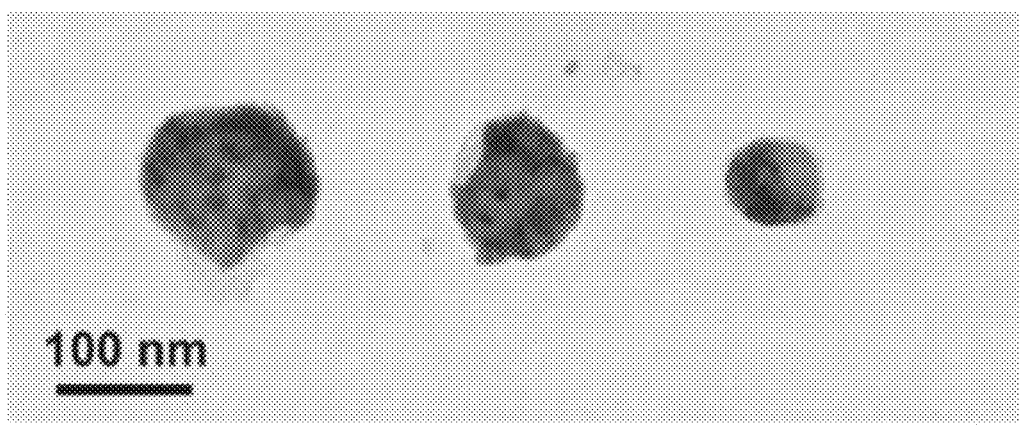
Figure 2C:
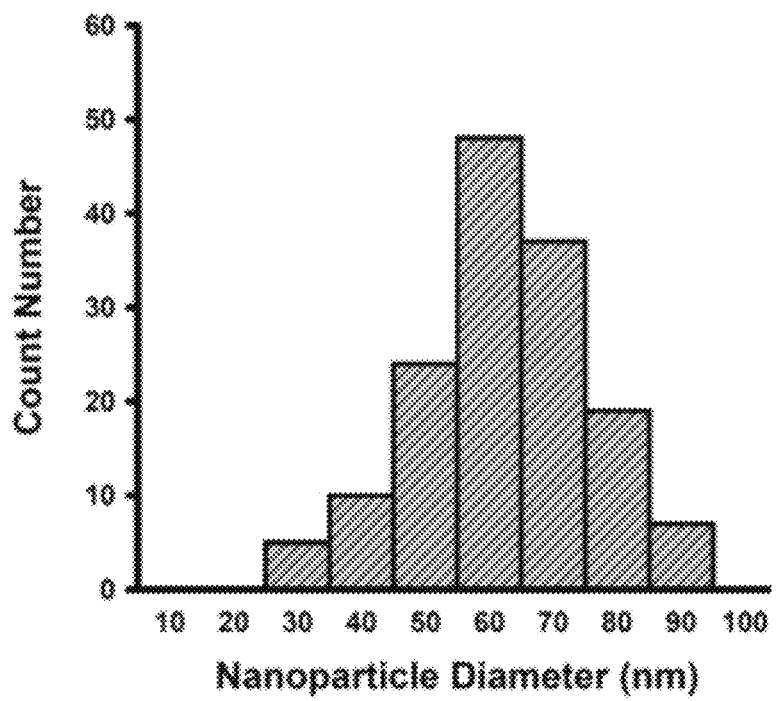
Figure 2D:
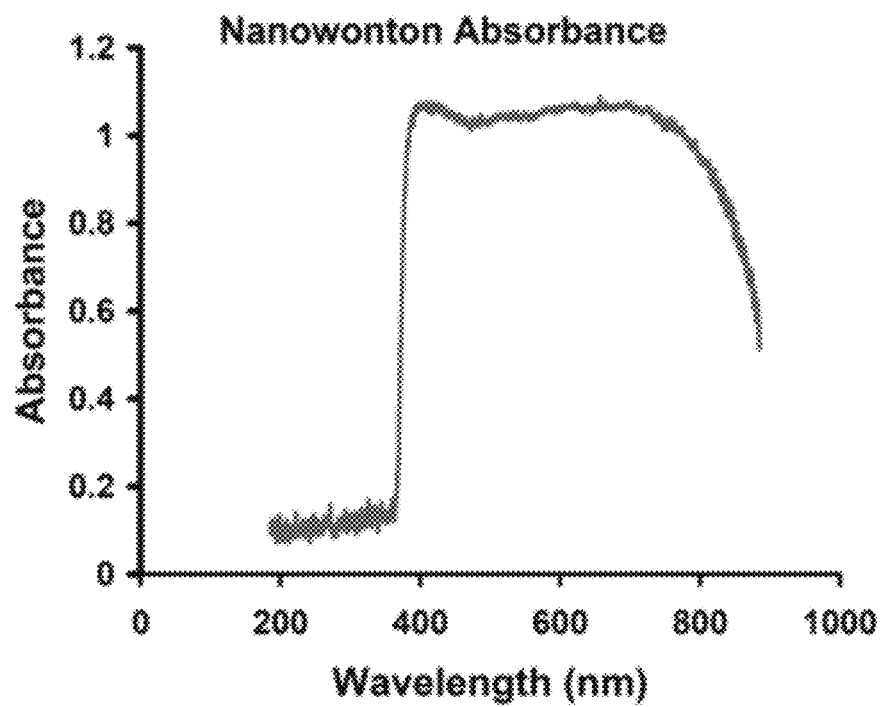
Figure 2E:
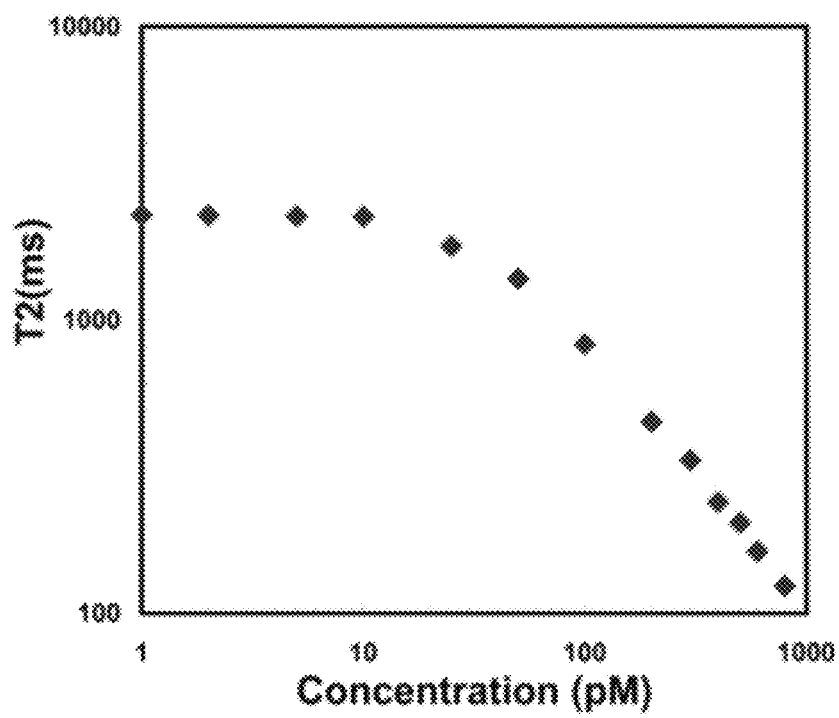

In various embodiments, methods of fabricating the nanoparticle described herein are provided. One schematic diagram of an illustrative fabrication process is shown in FIG. 1. In general, the fabrication process involves providing a substrate comprising a plurality of features, where each feature (or a plurality of the features) provides/presents a convex surface raised above the substrate. Then layers are deposited on the convex surface to form a nanoparticle. The layers comprise, in order, one or more first biocompatible layers; followed by one or more inner core material layers; followed by one or more second biocompatible layers. Then an etch (or other separation method) is performed that separates the nanoparticles from the convex surface.

In certain embodiments a sacrificial layer (e.g. a chromium layer) is deposited on the convex surface before depositing the first biocompatible layer(s). In certain embodiments the sacrificial layer is formed by depositing the sacrificial layer material at an angle with respect to an axis of the feature(s) while rotating the substrate, the sacrificial material layer forming the substantially convex surface. In various embodiments the sacrificial layer comprises one or more elements from IB, group II, group III, group IV, group V, group VI, group VII, or group VIII. In certain embodiments the sacrificial layer comprises a material (e.g., transition metal, semiconductor material) used in semiconductor fabrication processes. In certain embodiments the sacrificial layer comprises a material such as cromium, molybdenum, tungsten, copper, nickel, cobalt, and the like.

The various material layers can be deposited by any convenient method. such methods include for example, thin film deposition methods such as chemical deposition methods (e.g., plating, chemical solution deposition (CSD), chemical vapor deposition (CVD), and plasma enhanced chemical solution deposition (PECVD), and the like), physical deposition methods (e.g., thermal evaporation, sputtering, pulsed laser deposition, and cathodic arc deposition (arc-PVD), and the like), and other methods (e.g., molecular beam epitaxy, reactive sputtering, topotaxy, and the like). Such methods, and others, are well known to those of skill in the art (see, e.g., Seshan, (2002) *Handbook of Thin-Film Deposition Processes and Techniques—Principles, Methods, Equipment and Applications* (2nd Edition). William Andrew Publishing/Noyes).

Similarly, any of a number of methods can be used to provide a substrate comprising a plurality of features, where each feature (or a plurality of the features) provides/presents a convex surface raised above the substrate. For example, a substrate comprising a plurality of nanopillars, nanospheres, nanowires, nanotubes, and so forth can simply be etched, or such features can be deposited. In various embodiments, known methods of assembling nanoparticles on surface such as silicon (see, Liu and Green (2004) *J. Mater. Chem.*, 14: 1526) or polymers (see, e.g., Lu et al. (2005) *Nano Lett.* 5: 5) as well as E-beam fabricated nanoparticle arrays (see, e.g., Liao et al. (1981) *Chem. Phys. Lett.* 82: 355) can be utilized. In certain embodiments, the nanoparticles can be preformed and electrostatically, theremally, ionically or chemically affixed to an underlying surface. In various embodiments the nanoparticles can include nanopillars, nanorods, nanopyramids, nanowires, nanospheres, a nanocrescents, nanohorns, nanotubes, nanotetrepods, a single- or multi-layered nanodisks, and the like. Any of a number of materials can be used as the substrate and/or nanofeatures. Desirably, the substrate and/or nanofeatures are fabricated from a material that can be etched/dissolved without damaging the nanoparticle(s). In certain embodiments the substrate/nanofeatures can be resistant to dissolution, but can be provided with a sacrificial layer that can be dissolved to release the formed nanoparticles.

Suitable materials for the substrate include, for example, glass, silicon, polysilicon, polymer substrates, graphite substrates, graphene substrates and the like. In various embodiments the nanofeatures range in size from 1, 2, 5, 10, 20, 30, or 40 nm to about 200 nm, more preferably from about 1, 2, 5, 10, 20, 30, or 40 nm to about 100 nm, still more preferably from about 1, 2, 5, 10, 20, 30, or 40 nm to about 50 or 80 nm. In various embodiments the average spacing between nanofeatures ranges from about 2 nm to about 100 nm, still more preferably from about 4 nm to about 50 or 80 nm. In one illustrative embodiment, the nanoscale features have an average dimension (e.g. diameter) of about 20 nm and an average spacing of about 40 to about 50 nm. In certain embodiments the nanoscale features have a center to center distance that ranges from about 10, 15, 20, or 25 nm to about 100, 150, 200, 250, 300, 350, 400, 450, or 500 nm. In certain embodiments the center to center distance of the features ranges from about 50 or 75 nm to about 100 nm, 150 nm, or 200 nm.

Optionally, a convex surface can be formed on top of the nanofeatures on the substrate. One illustrative method of forming such a convex surface is heating and reannealing of the substrate.

In various embodiments the layer deposition results in depositing the layers on the convex surface(s) of at least a plurality of features, thereby forming the precursor of a plurality of nanoparticles. The etching/separation step then produces a population of nanoparticles.

A schematic diagram of the fabrication procedure used to produce the nanoparticles described in Example 1 is illustrated in FIG. 1. First, a batch-fabricated vertical silicon nanopillar array was fabricated on the surface of a 4-inch diameter silicon wafer. Starting with a single crystal silicon wafer, a 300 nm thick thin layer of poly-crystal silicon is deposited on the polished top surface of the silicon wafer. The silicon wafer is etched in a plasma-assisted reactive ion etcher.

The etching process to make the nanopillars is different from those used in conventional silicon film etching. At first, the native oxide layer on the poly film is stripped off by using $SF_6$ plasma etching for 10 seconds. Next, a mixture of $O_2$ and HBr gases is flowed in the RF plasma etching chamber for 7 seconds to define nanoscale oxide islands on the top of poly silicon film surface. These nanoscale oxide islands are created by the simultaneous etching and oxidation process. The average diameter of the oxide islands was about 20 nm and the spacing distance between adjacent oxide islands was dependent on the mixing ratio of $O_2$ and HBr. Then the poly silicon film is etched by pure HBr plasma for 10~20 seconds to form short nanopillar arrays. As the nanoscale oxide islands serve as the etching mask (because it's more resistive to etching), the nanopillar etching has excellent directionality. Finally, the oxide island layer is removed by $SF_6$ plasma etching and the silicon nanopillars are exposed. The coverage of the nanopillar structure was more than 90% of the total wafer surface area. On the top of each silicon nanopillar, there was a spherical silicon oxide nanostructure, which was formed by heating and reannealing of the wafer to have a semiround shape of silicon oxide on the nanopillar top.

Four metallic layers of 5 nm chromium, 10 nm gold, 10 nm cobalt and 10 nm gold were sequentially deposited on the wafer surface, through vapor deposition or sputtering of metal using magnetron vapor deposition machine. The gold layers encapsulate the cobalt core, so the cobalt core is not exposed to living tissue, nor to oxidation in the air. Thin layers of gold can be deposited on the silicon wafer surface using electron beam evaporation. Depending on the energy of the electron beam, the deposition rate can be as low as a couple of angstrom per second. However, the original deposited gold layer tends to be particulate. After thermal annealing in nitrogen-flow high temperature oven, the gold nanoparticles on top of the nanopillars become smooth and semi-spherical at the side not blocked by the nanopillars. However, after deposition, the side-walls of all the nanopillars remained exposed. The silicon wafer was therefore immersed in a 10% KOH bath solution at 80° C., etching away the nanopillars from the unprotected sidewalk in 10 minutes. The multilayer metallic nanostructure on the top of the nanopillars was lifted off and suspended in the KOH bath solution. Since silicon oxide and chromium were also etched away by KOH, only the gold-cobalt-gold sandwich nanostructures, the nanowontons, remained in solution. These were finally separated by centrifugation.

These fabrication methods are illustrative and not limiting. Using the teachings provided herein, nanowonton nanoparticles comprising other dimensions and/or materials can be produced by one of skill in the art.

Targeted Nanoparticles.

Targeting Ligands.

In various embodiments the nanoparticles described herein can be attached to one or more ligands to facilitate targeting (e.g., binding and/or internalization and/or preferential delivery and/or local concentration) to a particular cell, cell type, tissue, organ, and the like.

Targeting ligands are ligands that bind, in certain embodiments, preferentially and/or specifically bind a component characteristic of a particular cell, cell type tissue, organs, or region. Illustrative targeting ligands include proteins such as polyclonal or monoclonal antibodies, antibody fragments, or chimeric antibodies, enzymes, or hormones, or sugars such as mono-, oligo- and poly-saccharides, nucleic acids (e.g., RNA, DNA, etc.), and the like.

In certain preferred embodiments, the targeting moiety is a moiety that binds a cancer marker e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention,* 22(2): 147-152). Other important targets for are membrane bound complement regulatory glycoprotein: CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HUB 45 marker. Non-hodgkins lymphomas have been characterized by the CD20, CD19, and Ia marker, And various prostate cancers have been characterized by the PSMA and SE10 markers.

In addition, many kinds of tumor cells display unusual antigens that are either inappropriate for the cell type and/or its environment, or are only normally present during the organisms' development fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies. Nanoparticles attached to anti-disialoganglioside GD2 monoclonal antibodies can be used to aid targeting of the nanoparticles to cells expressing the tumor antigen for visualization and/or treatment.

In another non-limiting example, breast and gynecological cancer antigen specific antibodies are described in U.S. Pat. No. 5,939,277. In a further non-limiting example, prostate cancer specific antibodies are disclosed in U.S. Pat. No. 6,107,090. Thus, it is contemplated that the antibodies as would be known to one of ordinary skill in the art may be used to target the nanoparticles described herein to specific tissues and cell types. In certain embodiments of the invention, contemplated targeting ligands interact with integrins, proteoglycans, glycoproteins, receptors or transporters. Suitable ligands include, but are not limited to any that are specific for cells of the target organ, or for structures of the target organ exposed to the circulation as a result of local pathology, such as tumors.

Other kinds of tumor cells display cell surface receptors that are rare or absent on the surfaces of healthy cells, and which are responsible for activating cellular signaling pathways that cause the unregulated growth and division of the tumor cell. Examples include (ErbB2). HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table I. Antibodies to these and other cancer markers are known to those of skill in the art and can be obtained commercially or readily produced, e.g. using phage-display technology.

TABLE 1

Illustrative cancer markers and associated references, all of which are incorporated herein by reference for the purpose of identifying the referenced tumor markers.

| Marker | Reference |
|---|---|
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmann et al. (1997) *Oncol Res.*, 9(3) 119-127 |
| APRIL | Sordat et al. (1998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-abl (b3a2) | Verfaillie et al. (1996) *Blood*, 87(11): 4770-4779 |

TABLE 1-continued

Illustrative cancer markers and associated references, all of which are incorporated herein by reference for the purpose of identifying the referenced tumor markers.

| Marker | Reference |
|---|---|
| CA-125 | Bast et al. (1998) *Int J Biol Markers*, 13(4): 179-187 |
| CASP-8/FLICE | Mandruzzato et al. (1997) *J Exp Med.*, 186(5): 785-793. |
| Cathepsins | Thomssen et al. (1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al. (1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al. (1996) *Melanoma Res.*, 6(1): 11-24 |
| gp75/TRP-1 | Lewis et al. (1995) *Semin Cancer Biol.*, 6(6): 321-327 |
| hCG | Hoermann et al. (1992) *Cancer Res.*, 52(6): 1520-1524 |
| Heparanase | Vlodavsky et al. (1999) *Nat Med.*, 5(7): 793-802 |
| Her2/neu | Lewis et al. (1995) *Semin Cancer Biol.*, 6(6): 321-327 |
| Her3 | |
| HMTV | Kahl et al. (1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/MART-1 | Lewis and Houghton (1995) *Semin Cancer Biol.*, 6(6): 321-327 |
| mesothelin | Chang et al. (1996) *Proc. Natl. Acad. Sci., USA*, 93(1): 136-140 |
| MIC A/B | Groh et al. (1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |

TABLE 1-continued

Illustrative cancer markers and associated references, all of which are incorporated
herein by reference for the purpose of identifying the referenced tumor markers.

| Marker | Reference |
| --- | --- |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci., USA*, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al. (1997) *Cancer Res.*, 57(12): 2321-2324 |
| RAGE-1 | Gaugler et al. (1996) *Immunogenetics*, 44(5): 323-330 |
| Rb | Dosaka-Akita et al. (1997) *Cancer*, 79(7): 1329-1337 |
| RCAS1 | Sonoda et al. (1996) *Cancer*, 77(8): 1501-1509. |
| SART-1 | Kikuchi et al. (1999(*Int J Cancer*, 81(3): 459-466 |
| SSX gene family | Gure et al. (1997) *Int J Cancer*, 72(6): 965-971 |
| STAT3 | Bromberg et al. (1999) *Cell*, 98(3): 295-303 |
| STn (mucin assoc.) | Sandmaier et al. (1999) *J Immunother.*, 22(1): 54-66 |
| TAG-72 | Kuroki et al. (1990)*Cancer Res.*, 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prey*, 7(6): 497-504 |
| Thymosin β 15 | Bao et al. (1996) *Nature Medicine.* 2(12), 1322-1328 |
| IFN-α | Moradi et al. (1993) *Cancer*, 72(8): 2433-2440 |
| TPA | Maulard et al. (1994) *Cancer*, 73(2): 394-398 |
| TPI | Nishida et al. (1984) *Cancer Res* 44(8): 3324-9 |
| TRP-2 | Parkhurst et al. (1998) *Cancer Res.*, 58(21) 4895-4901 |
| Tyrosinase | Kirkin et al. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et al. (1995) *Oncogene* Aug. 17, 1995; 11(4): 635-645 |
| Glutathione S-transferase | Hengstler (1998) et al. *Recent Results Cancer Res.*, 154: 47-85 |

Any of the foregoing markers can be used as targets for targeting ligands attached to the nanowonton nanoparticles described herein. In certain embodiments the target markers include, but are not limited to, members of the epidermal growth factor family (1,e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Len-M1, MUC1, PMSA, TAG-72, phosphatidyl serine antigen, and the like.

The foregoing markers are intended to be illustrative and not limiting. Other tumor associated antigens will be known to those of skill in the art.

Attachment of Targeting Ligands.

The targeting ligands can be attached to the nanoparticle by any of a number of methods well known to those of skill in the art. Where the biocompatible outer layers comprise gold, the nanoparticle can readily be attached to a targeting ligand by providing the ligand with an SH group that will react with the gold. In such cases, the ligand can natively provide an SH group, or it can be functionalized to provide an SH group.

In various embodiments the targeting ligands and the nanoparticle(s) can be conjugated via a single linking agent or multiple linking agents. For example, the targeting moiety and the nanoparticle(s) can be conjugated via a single multi-functional (e.g., bi-, tri-, or tetra-) linking agent or a pair of complementary linking agents. In another embodiment, the targeting moiety and the nanoparticle(s) are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine (NH$_2$), hydroxyl (—OH), aldehyde (—CHO), alcohol (ROH), ketone (R$_2$CO), active hydrogen, ester, sulfhydryl (SH), phosphate (—PO$_3$), or photoreactive ligands, Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric ligands include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins: Advances in Chemistry Series*, Vol. 198, American Chemical Society, Washington, D.C.

A "linker" or "linking agent" as used herein, is a molecule that is used to join two or more molecules. In certain embodiments the linker is typically capable of forming covalent bonds to both molecule(s) (e.g., the targeting moiety and the nanoparticle(s)). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids.

A bifunctional linker having one functional group reactive with a group on one molecule (e.g., a targeting peptide), and another group reactive on the other moiety (nanoparticle), can be used to form the desired conjugate. Alternatively, derivatization can be performed to provide functional groups. Thus, for example, procedures for the generation of free sulfhydryl groups on peptides are also known (See U.S. Pat. No. 4,659, 839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075).

Methods of Imaging and/or Treatment.

In various embodiments, the nanoparticles described herein are used in methods of imaging and/or treatment. Typically, in such methods, the nanoparticles are loaded into a cell, tissue, organ, or organism. The cell, tissue, organ or organism can then be subject to one or more imaging modalities (e.g., MRI, PET, PAT, SPECT, etc.) and the nanoparticles detected to aid the visualization of the target cell, tissue, organ, and the like. Where therapeutic modalities are desired, the nanoparticles, e.g., once visualized at the desired location, are subject to a regime that induces particle heating (hyperthermic therapies), and/or light or radiation emission (e.g., photodynamic therapy (PDT)), and/or subject to conditions that degrade the biocompatible outer layer(s) thereby releasing the contents of the nanoparticles (e.g., radioactive materials, cytotoxins, drugs, etc.)

The nanoparticles described herein may be administered/delivered to the target cell or tissue, organ, or organism sing targeting schemes involving specific chemical interactions (e.g., antigen-antibody binding, etc.) to preferentially associate the nanoparticles with the target cell, tissue, organism, etc., or the administration may consist of the simple delivery of the nanoparticles to the desired area or tissue, for example by the delivery of a pharmaceutical/imaging composition comprising the nanoparticles described herein.

The nanoparticles may be directed to the surface of the subject cells tissue, or organ, or they many be directed to interior sites of the cells, organs, and/or tissue(s).

The nanoparticles can be formulated as imaging and/or therapeutic reagents for administration via any of a large number of modalities. Various types of formulations can be used depending on the desired form of administration.

In certain embodiments the nanoparticles are formulated into aqueous or aqueous-compatible composition. Such compositions typically comprise an effective amount of nanoparticles dissolved and/or dispersed and/or suspended in a carrier (e.g., a pharmaceutically carrier or medium). When used as an imaging reagent an effective amount is an amount sufficient to produce a detectable signal and preferably an optimal signal for one or more detection or imaging modalities. When used a therapeutic reagent, an effective amount is an amount sufficient to produce the desired therapeutic effect at the target cell, tissue, or organ.

In various embodiments the nanoparticles are dissolved in, dispersed in, or otherwise suspended in a pharmaceutically acceptable carrier. As used herein, the terms "pharmaceutically and/or pharmacologically acceptable" refer to molecular entities and/or compositions that do not produce substantial adverse, allergic and/or other deleterious effects when administered to an animal, as appropriate. As used herein, "pharmaceutically acceptable carrier" includes, but is not limited to solvents, dispersion media, coatings, antibacterial agents, antifungal agents, isotonic and/or absorption delaying agents and the like. The use of pharmaceutically acceptable carrier is well known in the art. The pharmaceutical composition can further comprise supplementary active ingredients.

In certain embodiments, the pharmaceutical composition is formulated for parenteral administration, e.g., formulated for injection via the intravenous, intramuscular, sub-cutaneous, intralesional, and/or intraperitoneal routes. Typically, such compositions are prepared either as liquid solutions or suspensions. Solid forms suitable for using to prepare solutions and/or suspensions upon the addition of a liquid prior to administration can also be prepared; and, in various embodiments, the preparations can also be emulsified.

In various embodiments the nanoparticles or targeted nanoparticles described herein can be formulated into a composition in a neutral and/or salt form. Any pharmaceutically acceptable salt known to a person skilled in the art can be used, providing it would not interfere with the function of the nanoparticles.

Sterile injectable solutions can be prepared by incorporating the active compounds, specifically the nanoparticles in the required amount in the appropriate solvent/carrier, optionally with other ingredients as detailed above, as required. Generally, dispersions are prepared by incorporating the various sterilized active ingredients into a sterile vehicle that contains the basic dispersion medium and/or the required other ingredients. In the case of sterile powders for the preparation of sterile injectable solutions, in certain embodiments the components (e.g., nanoparticles) are prepared via vacuum-drying and/or freeze-drying techniques to yield a powder of the active ingredient plus any additional desired ingredient from a previously sterile solution thereof. The preparation of more, and/or highly, concentrated solutions for direct injection is also contemplated.

Upon formulation, nanoparticle formulations are administered in a manner compatible with the dosage formulation and/or in such amount as is diagnostically and/or therapeutically effective. The formulations are easily administered in a variety of dosage forms, such as the type of injectable solutions described above, but drug release capsules and/or the like can also be employed.

Other pharmaceutically acceptable forms of nanoparticle composition include, for example, tablets and/or other solids for oral administration; liposomal formulations; time release capsules; and/or any other form currently in use, including creams and gels. One may also use nasal solutions and/or sprays, aerosols and/or inhalants to deliver the nanoparticle compositions described herein. Nasal and inhalation formulations are often aqueous solutions designed to be administered to the nasal passages, oral cavity, throat or lungs in drops and/or sprays.

Additional formulations suitable for other modes of administration include, but are not limited to vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides.

Other delivery methods involve compositions comprising one or more lipids or liposomes associated with at least one nanoparticle.

A skilled artisan realizes that the systems and methods described herein can be employed in a variety of types of experimental, therapeutic and diagnostic procedures, including in vitro or in vivo experimental procedures.

In various embodiments the systems and methods described herein can be applied to a cell or a tissue, wherein the cell can be part of a tissue, such as a tumor tissue. In certain embodiments, the cell can, but is not limited to, at least one skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and any cancers thereof.

In certain embodiments the nanoparticle can be used to image and/or treat any cell or tissue including, but not limited to adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, small intestine, spleen, stem cells, stomach, testes or ascite tissue, and all cancers thereof.

certain embodiments various in vivo assays involve the use of various animal models, including transgenic animals that have been engineered to have specific defects, or early markers that can be used to measure the ability of the systems and methods described hereinto effect different cells or tissues within the organism. Due to their size, ease of handling, and information on their physiology and genetic make-up, mice and rats are well suited model systems, especially for transgenics. However, other animals are suitable as well, including rats, rabbits, hamsters, guinea pigs, gerbils, woodchucks, cats, dogs, sheep, goats, pigs, cows, horses and monkeys chiding chimps, gibbons and baboons).

Kits.

In another embodiment this invention provides kits for practice of the methods described herein. The kits typically comprise a container containing nanoparticles as described herein. In certain embodiments the nanoparticles are provided in a dry (e.g., lypholilized form). In certain embodiments, the nanoparticles are provided in a solution, suspension, colloid, or gel. In certain embodiments the nanoparticles are provided in a pharmaceutically acceptable carrier.

In various embodiments the kits, optionally include devices (e.g., syringe, swab, etc.) and or reagents (e.g., diluents and/or buffers) for administration of the nanoparticles to a biological subject or sample.

In addition, the kits optionally include labeling and/or instructional materials providing directions (i.e., protocols) for the practice of the methods described herein. In certain embodiments the instructional materials describe the use nanoparticles are described herein are imaging reagents.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media. (e.g., CD ROM), and the like. Such media may include addresses to internet sites that provide such instructional materials.

EXAMPLES

The following examples are offered to illustrate, but not to limit the claimed invention.

Example 1

Picomolar Sensitivity MRI and Photoacoustic Imaging of Cobalt Nanoparticles

Multimodality imaging based on complementary detection principles has broad clinical applications and promises to improve the accuracy of medical diagnosis. This means that a tracer particle advantageously incorporates multiple functionalities into a single delivery vehicle. In the present work, we explore a unique combination of MRI and photoacoustic tomography (PAT) to detect picomolar concentrations of nanoparticles. The nanoconstruct consists of ferromagnetic (Co) particles coated with gold (Au) for biocompatibility and a unique shape that enables optical absorption over a broad range of frequencies. The end result is a dual-modality probe useful for the detection of trace amounts of nanoparticles in biological tissues, in which MRI provides volume detection, whereas PAT performs edge detection.

We have synthesized nanoparticles for dual-modality (Al-Jamal and Kostarelos (2007) *Nanomedicine-UK*, 2: 85-98; Jaffer et al. (2006) *Mol Imaging* 5: 85-92; Mulder et al. (2005) *FASEB J.*, 19: 2008-2010; Tan and Zhang (2007) *J. Nanosci. Nanotechno.*, 7: 2389-2393; Dosev et al. (2007) *Nanotechnology* 18: 055102; Prinzen et al. (2007) *Nano Lett.*, 7: 93-100; Medarova al. (2006) *Int J Cancer* 118: 2796-2802) MRI and photoacoustic tomography (PAT). The incorporation of MRI and PAT into a single probe offers the unique possibility of combining the complementary strategies of contrast based volume imaging and edge detection. Our nanoconstruct consists of zero-valence ferromagnetic cobalt (Co) particles (Bala et al. (2004) *J Mater Chem* 14: 1057-1061) with a gold (Au) coating for biocompatibility and a unique shape rendering increased optical absorption over a broad range of frequencies (Hoelen et al. (1998) *Opt Lett* 23: 648-650; Oraevsky et al. (1997) *Appl Optics* 36: 402-415; Kruger et al. (1995) *Medical Physics* 22: 1605-1609; Andreev et al. (2003) *IEEE T. Ultrason. Ferr.* 50: 1383-1390; Kolkman et al. (2003) *IEEE J. Sel. Top. Quant.* 9: 343-346; Wang et al. (2004) *Opt. Lett.*, 29: 730-732; Wang et al. (2003) *Opt. Lett.*, 28: 1739-1741; Ku et al. (2004) *Physics in Medicine and Biology* 49: 1329-1338; Ku et al. (2005) *Appl. Optics*, 44: 770-775; Wang et al. (2003) *Nat. Biotechnol.*, 21: 803-806; Wang et al. (2004) *Nano Lett.*, 4: 1689-1692). This research theme follows the rapid developments in nanotechnology, diagnostic radiology, and targeted molecular imaging (Wickline and Lanza (2002) *J. Cell Biochem.*, 90-97), whereby nanoparticulate contrast agents, with the desirable properties of high chemical specificity, biocompatibility, and a reasonable half-life, are administered within a specific region of interest, nanoparticle-based imaging studies, higher particle concentrations lead to better signal-to-noise contrasts, but this also poses a tradeoff with the toxicity. Therefore, one of the most important parameters when developing particle-based contrast is the safest and lowest nanoparticle concentration that offers sufficient contrast sensitivity.

Introduction.

In MRI, magnetic materials such as gadolinium chelates and magnetic nanoparticles are often used (Cunningham et al. (2005) *Magnet. Reson. Med.*, 53: 999-1005; Kim et al. (2001) *J. Magn. Magn. Mater.*, 225: 256-261; Lu et al. (2006) *Nanotechnology* 17: 5812-5820) to enhance image contrast. The magnetic nanoparticles are passivated by biocompatible coatings such as dextrin, citrate, polystyrene/divinylbenzene, and elemental gold. These coatings also detoxify the particles, resulting in enhanced lifetimes in vivo. Typical examples of magnetic nanoparticulate core-shell configurations include magnetite-dextrin, magnetite-silica (Lu et al. (2007) *Nano Lett.*, 7: 149-154) and iron-gold (Cho et al. (2006) *Nanotechnology* 17: 640-644).

Laser-based PAT (Hoelen et al. (1998) *Opt Lett* 23: 648-650; Oraevsky et al. (1997) *Appl Optics* 36: 402-415; Kruger et al. (1995) *Medical Physics* 22: 1605-1609; Andreev et al. (2003) *IEEE T. Ultrason. Ferr.* 50: 1383-1390; Kolkman et al. (2003) *IEEE J. Sel. Top. Quant.* 9: 343-346; Wang et al. (2004) *Opt. Lett.*, 29: 730-732; Wang et al. (2003) *Opt. Lett.*, 28: 1739-1741; Ku et al. (2004) *Physics in Medicine and Biology* 49: 1329-1338; Ku et al. (2005) *Appl. Optics*, 44: 770-775; Wang et al. (2003) *Nat. Biotechnol.*, 21: 803-806; Wang et al. (2004) *Nano Lett.*, 4: 1689-1692) is a hybrid imaging modality (see FIG. 6), It uses a pulsed laser source to illuminate a biological sample. Light absorption by the tissue results in a transient temperature rise on the order of 10 mK. The rapid thermoelastic expansion excites ultrasonic waves that are measured by using broadband ultrasonic transducers conformally arranged around the sample. Finally, a modified back-projection reconstruction algorithm (Xu and Wang (2005) *Phys. Rev. E*, 71: 016706) is used to construct a map of the distribution of the optical energy deposition within the sample. The spatial resolution of PAT is not limited by optical diffusion, but instead by the bandwidth of the acoustic detectors. It has been shown that PAT can depict subsurface tissue structures and functional changes noninvasively with resolution up to 100 μm (Wang et al. (2004) *Opt. Lett.*, 29: 730-732; Wang et al. (2003) *Opt. Lett.*, 28: 1739-1741).

Like other optical modalities, PAT is highly sensitive in mapping and quantifying the dynamic distribution of optical contrast agents such as metallic nanocolloids and organic dyes (Ku et al. (2004) *Physics in Medicine and Biology* 49: 1329-1338; Ku et al. (2005) *Appl. Optics*, 44: 770-775; Wang et al. (2003) *Nat. Biotechnol.*, 21: 803-806; Wang et (2004) *Nano Lett.*, 4: 1689-1692; Copland et al. (2004) *Mol. Imaging Biol.*, 6: 341-349).

Figure 7:
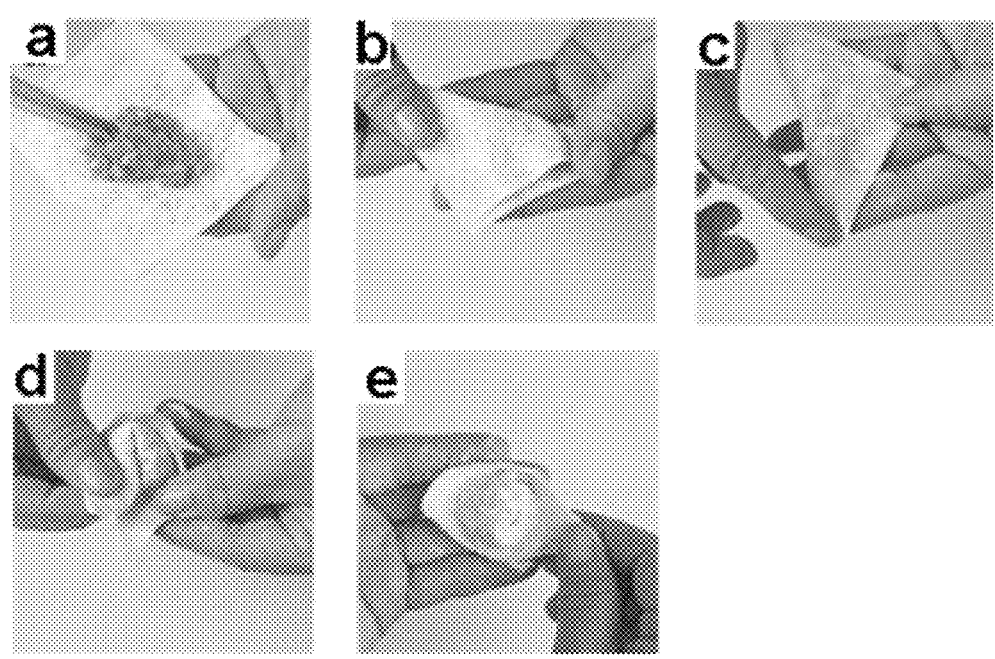
FIG. 7 illustrates a schematic of Chinese wonton.

In this example, we describe the fabrication of a composite-material nanoparticle, which we call "nanowonton." The nanowonton has a Co core and an Au thin-film coating and is a construct similar to the Chinese eatable called the wonton (see FIG. 1 and FIG. 7). The nanowontons have been characterized by scanning and transmission electron microscopies, absorption spectroscopy, and NMR relaxometry (FIG. 2). The nanowonton is shown to exhibit a combination of ferromagnetic and optical responses (FIG. 2), making it amenable to dual-modality MRI and PAT studies. NMR $T_2$ relaxivity measurements reveal a per-particle retaxivity of $1 \times 10^7$ s$^{-1}$ mM$^{-1}$ (Table 2).

TABLE 2

$T_2$ relaxivity per particle concentration is calculated to be $1 \times 10^7$ s$^{-1}$ mM$^{-1}$.

| Sample No | Conc. pM | $T_2$ ms | Conc. mM | $1/T_2$ s$^{-1}$ |
|---|---|---|---|---|
| 1 | 1,000 | 123 | 0.000001 | 8.1301 |
| 2 | 800 | 124 | 0.0000007 | 8.0645 |
| 3 | 600 | 163 | 0.0000006 | 6.1350 |
| 4 | 500 | 204 | 0.0000005 | 4.9020 |
| 5 | 400 | 239 | 0.0000004 | 4.1841 |
| 6 | 300 | 333 | 0.0000003 | 3.0030 |
| 7 | 200 | 451 | 0.0000002 | 2.2173 |
| 8 | 100 | 828 | 0.0000001 | 1.2077 |
| 9 | 50 | 1384 | 0.00000005 | 0.7225 |
| 10 | 25 | 1788 | 0.000000025 | 0.5593 |
| 11 | 10 | 2250 | 0.00000001 | 0.4444 |
| 12 | 5 | 2258 | 0.000000005 | 0.4429 |

TABLE 2-continued

T$_2$ relaxivity per particle concentration is calculated to be 1 × 10$^7$ s$^{-1}$ mM$^{-1}$.

| Sample No | Conc. pM | T$_2$ ms | Conc. mM | 1/T$_2$ s$^{-1}$ |
|---|---|---|---|---|
| 13 | 2 | 2268 | 0.000000002 | 0.4409 |
| 14 | 1 | 2270 | 0.000000001 | 0.4405 |

Figure 8:
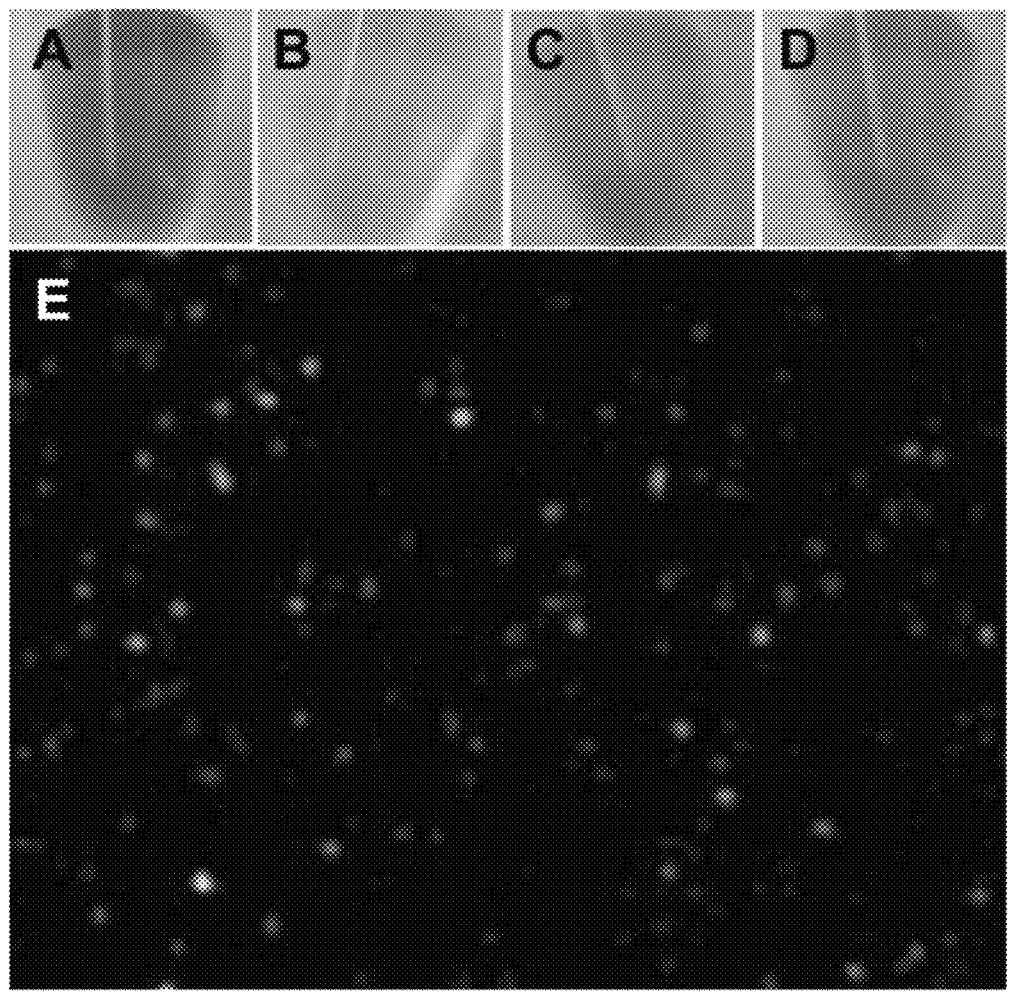
FIG. 8, panels A-E, show the tunability of scattering wavelength of nanowonton by changing the size of the nanowonton. Panel A: The nanowonton with exterior diameter of 60 nm used in the study. Panel B: 80 nm diameter nanowonton. Panel C: 40 nm nanowonton. Panel D: A 10 nm nanowonton, Panel E: Scattering light microscopy image of the 60 nm diameter nanowonton with 700 nm peak scattering wavelength used in the study.

Previously, the oxidation-induced instability and toxicity of Co nanoparticles have prohibited their wide use as MRI contrast agents, but in the present case, the Au coating circumvents this issue. Furthermore, the shape and thickness of the Au capping layer are designed so that the center of its optical absorption range matches the near infrared laser excitation wavelength used in PAT imaging (700 nm) optimizing the photothermal response. We have also reported the geometry-dependent optical absorption for similarly shaped nanostructures such as nanocrescents (Lu et al. (2005) *Nano Lett.*, 5: 119-124). The nanowonton design provides wavelength tunability for PAT (FIG. 8) and can be further improved through control of the fabrication procedure.

Figure 3B:
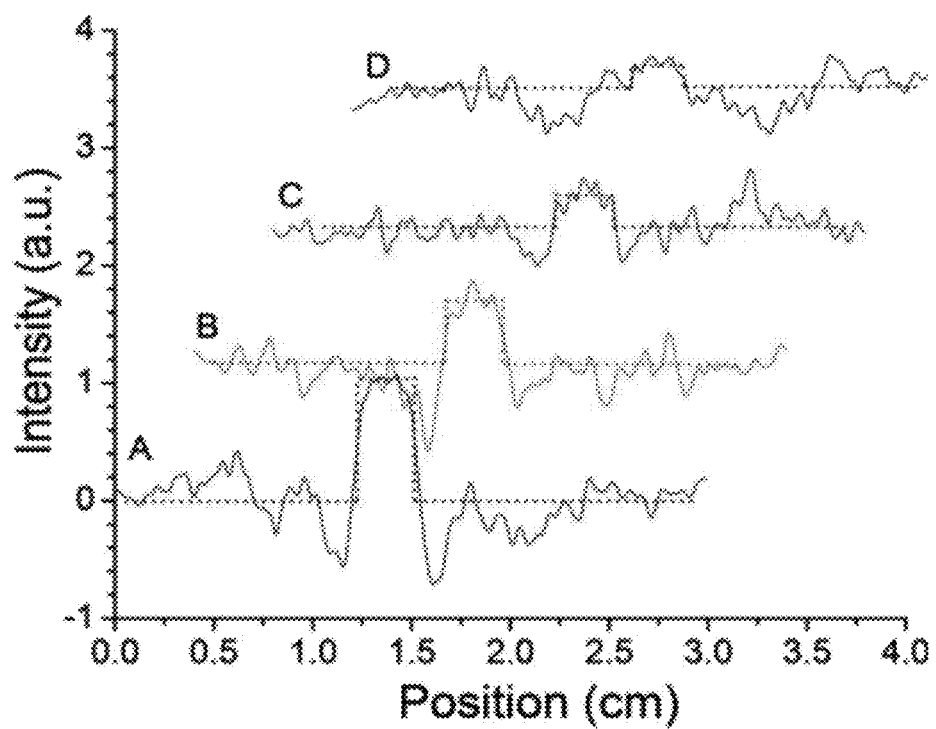
FIGS. 3A and 3B show photoacoustic (PAT) imaging of nanowonton phantom gets.
Figure 3A:
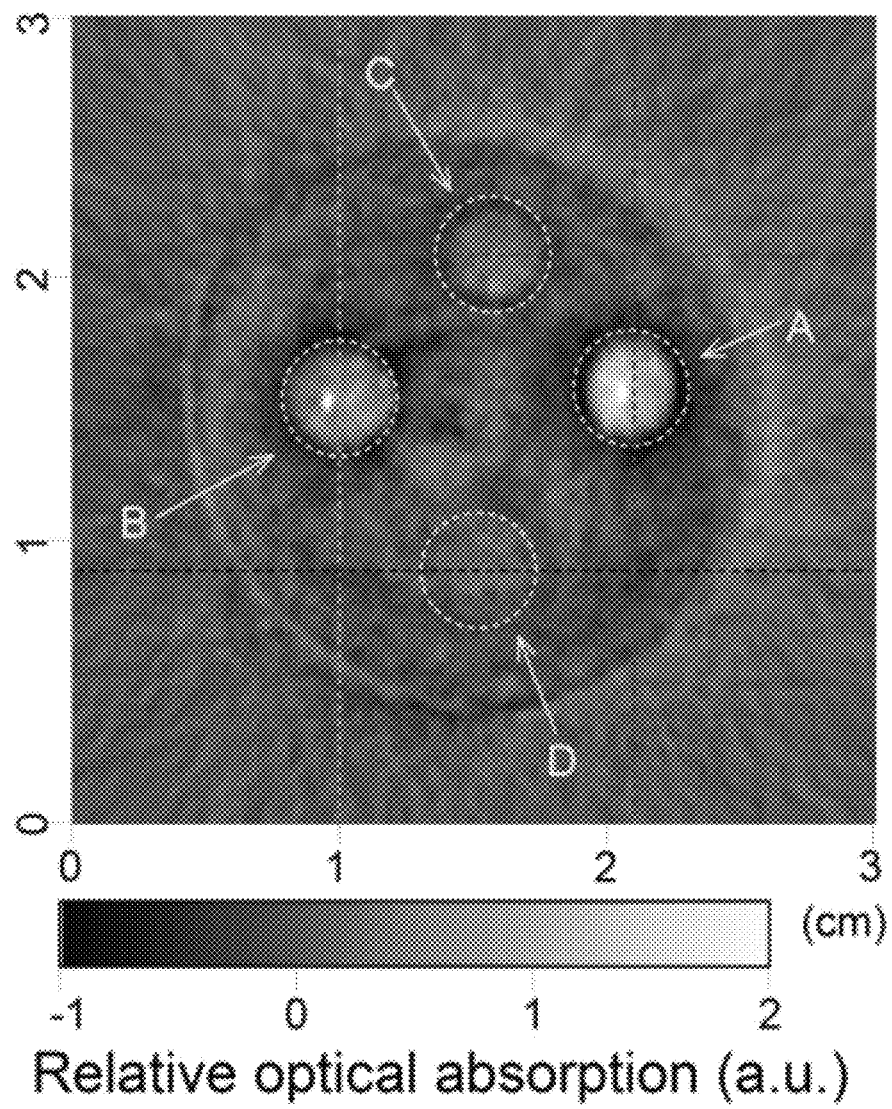
Figure 4A:
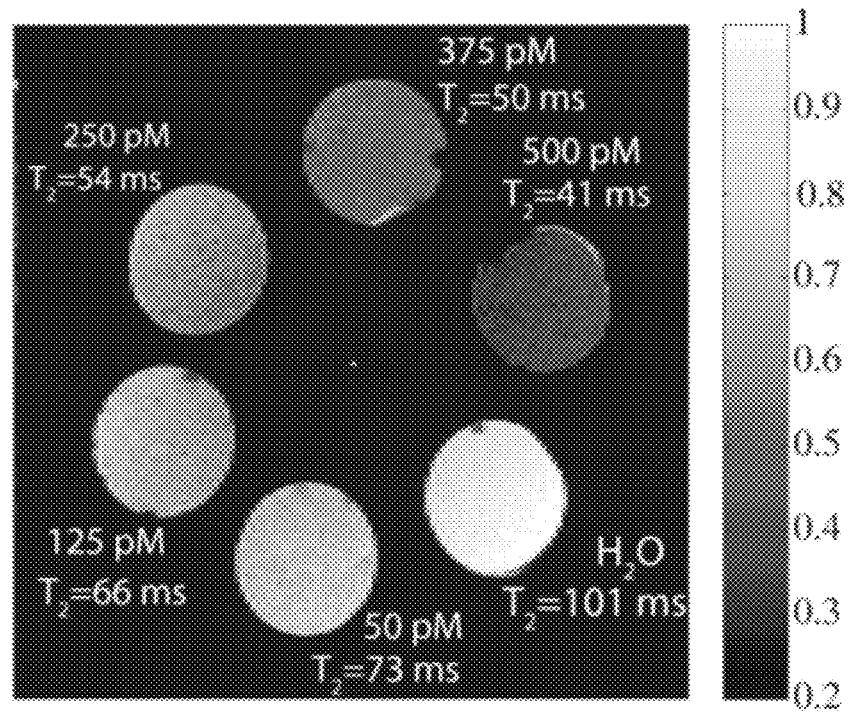
FIGS. 4A-4D show MRIs of nanowonton gel phantoms. The nanowonton gels are arranged along the perimeter of a circle.
Figure 4B:
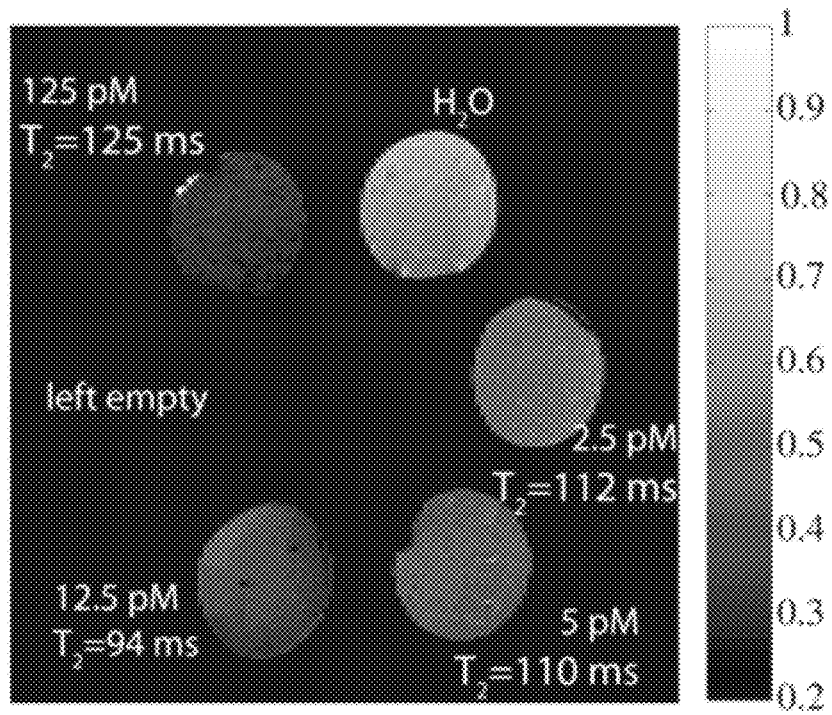
Figure 4C:
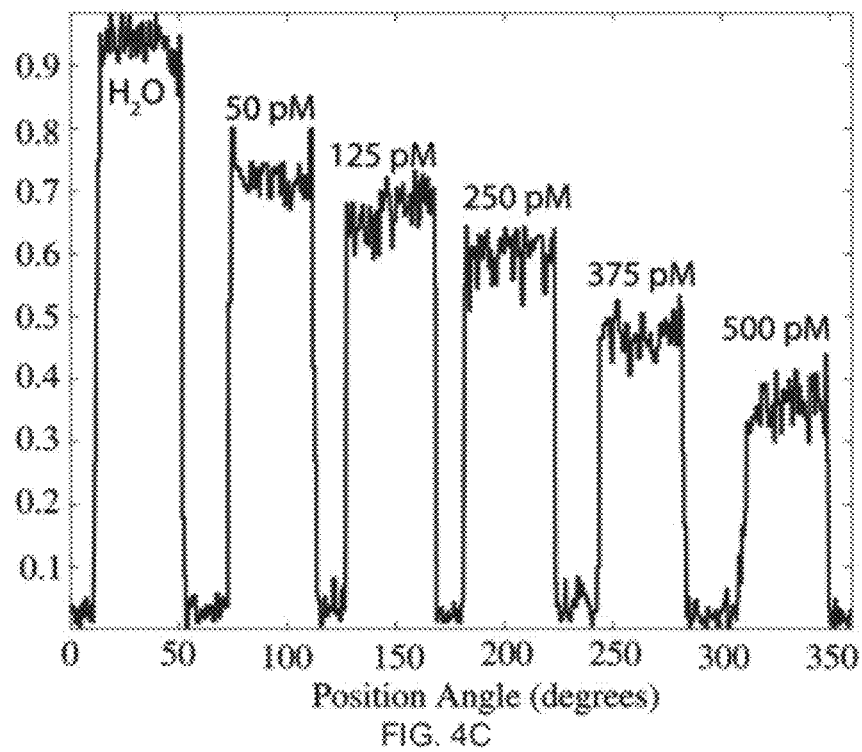
Figure 4D:
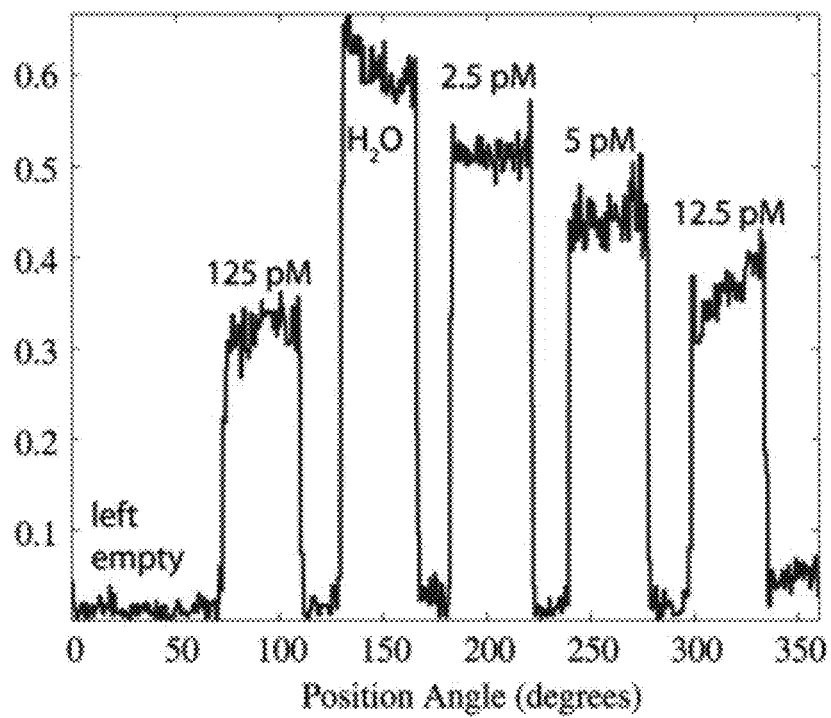

The PAT imaging contrast is demonstrated in FIG. 3A, for an porcine gel containing several inclusions of different nanowonton concentrations. The inclusion with a nanowonton concentration of 13 pM can hardly be recognized from the background, leading us to conclude that this PAT system has a detection sensitivity of the order of 25 pM. Spin echo MRI images of Co nanowonton agarose gel phantoms A and B are shown in FIGS. 4A and 4B, Spin echo images show that higher concentrations lead to shorter T$_2$ values for the water protons. The smallest detectable concentration is 2.5 pM and the contrast with respect to 5 pM is also clearly visible in FIGS. 4B and 4D.

Figure 5:
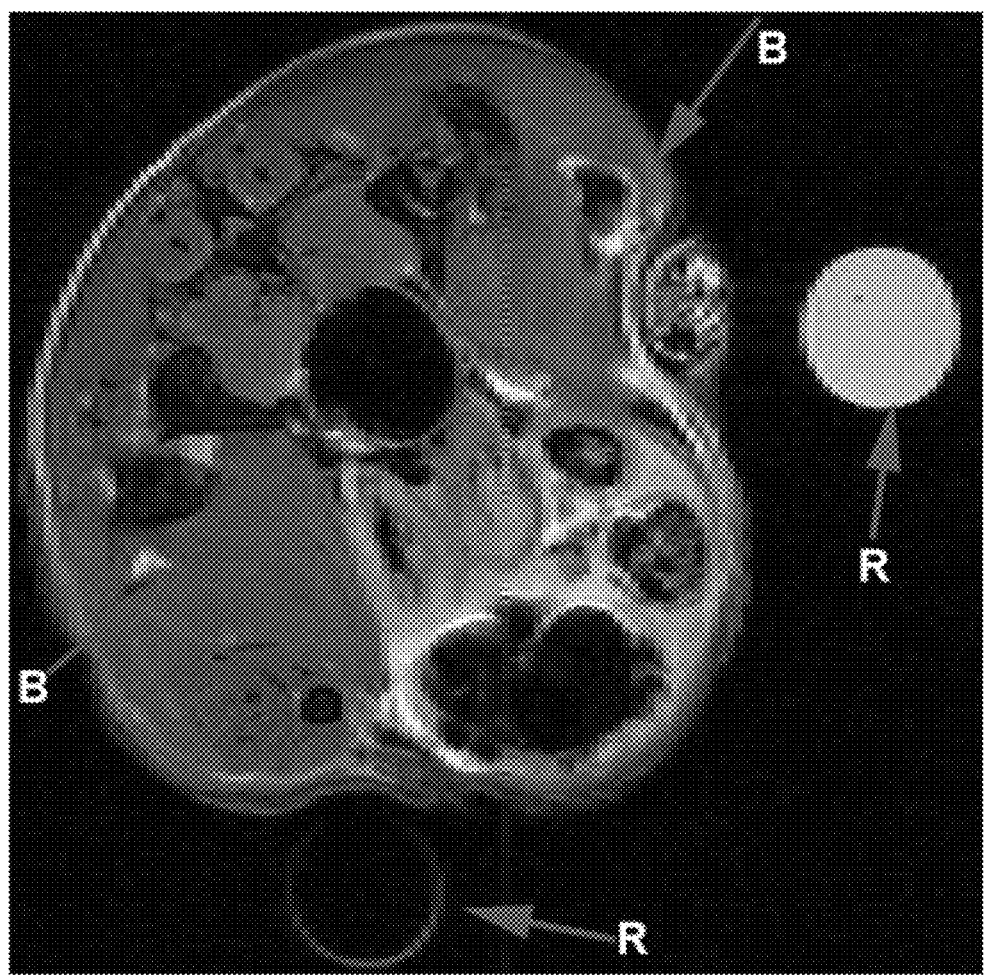
FIG. 5 shows a transverse (axial) MRI image in mouse leg muscle injected with Co nanoparticles in PBS solution. The position of the "B" arrows indicates the sites of injection for the Co nanoparticles (upper right corner) and the PBS control (lower left corner). Two water-carrying test tubes are also visible in the scans for purposes of MRI slice alignment ("R" arrows). MRI parameters were: TE=50 ms; TR=1 s; field of view is 2.6 cm×2.6 cm, and slice thickness is 0.5 mm.
Figure 9:
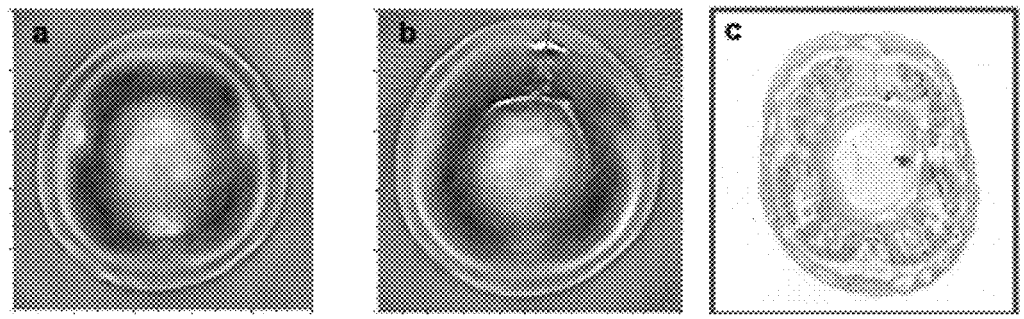
FIG. 9, panels A-C, illustrate photoacoustic imaging of rat tail joint taken (panel a) before and (panel b) after the administration of nanowonton contrast agent at 100 pM. For comparison purpose, we also have obtained the (panel c) histological photograph of a similar cross section showing the periosteum. In panels a and b, grayscale is in arbitrary units of relative optical absorption, and x y scales are 1 cm×1 cm.

A T$_2$-weighted spin echo image from a slice through the mouse's leg muscles is shown in FIG. 5. The injection of PBS-buffered Co nanoparticles at 50 pM concentration results in a substantial drop in the MR signal in this region whereas the control injection with PBS shows no such contrast enhancement. In FIG. 9, PAT images acquired before and after a rat tail injection show the type of contrast enhancement which can be expected from a local injection of 100 pM contrast agent. Because of high-frequency ultrasound detection, the PAT modality is generally better suited at delineating edges at the location of the contrast. These nanowonton particles advantageously combine the strengths of both MRI and PAT modalities into a single delivery vehicle.

This dual-modality PAT/MRI contrast agent demonstrates, so far, the most sensitive detection experiment of magnetic nanoparticles with particle concentrations in the picomolar and tens of picomolars range. The particles may even be used for stand-alone MRI or PAT. For example, in the MRI studies, the T$_2$ contrast is clearly visible to concentrations as low as 2.50 pM in phantoms and 50 pM in tissues. These detection thresholds are 7 orders of magnitude better than those demonstrated by Lu et al. (2006) *Nanotechnology* 17: 5812-5820, for monocrystalline iron oxide particles. Our T$_2$ relaxivity (see Table 2) per-particle concentration is 5 orders of magnitude better than the cited work. The particle relaxivity and T$_2$-weighted MRI detection threshold are also better than those demonstrated by Cho et al. (Cho et al. (2006) *Nanotechnology* 17: 640-644) for 18 nm-diameter Fe/Au nanoparticles. This degree of sensitivity is, to our knowledge, unprecedented and compares with sensitivities approaching those of radioactive labels. This improved performance is in large part contributed by our choice of a ferromagnetic material, cobalt, which has a saturation magnetization 3.42 times larger than magnetite, leading to a per-particle relaxivity that is nearly 12 times larger. Because T$_2$-weighted MRI depends exponentially on the relaxation rate, this leads to a substantial difference in contrast Observed in our experiments. We refer to the supplemental information section below for a more extensive discussion of relaxivity effects, including a comparison with results from other agents reported in the literature.

Figure 10:
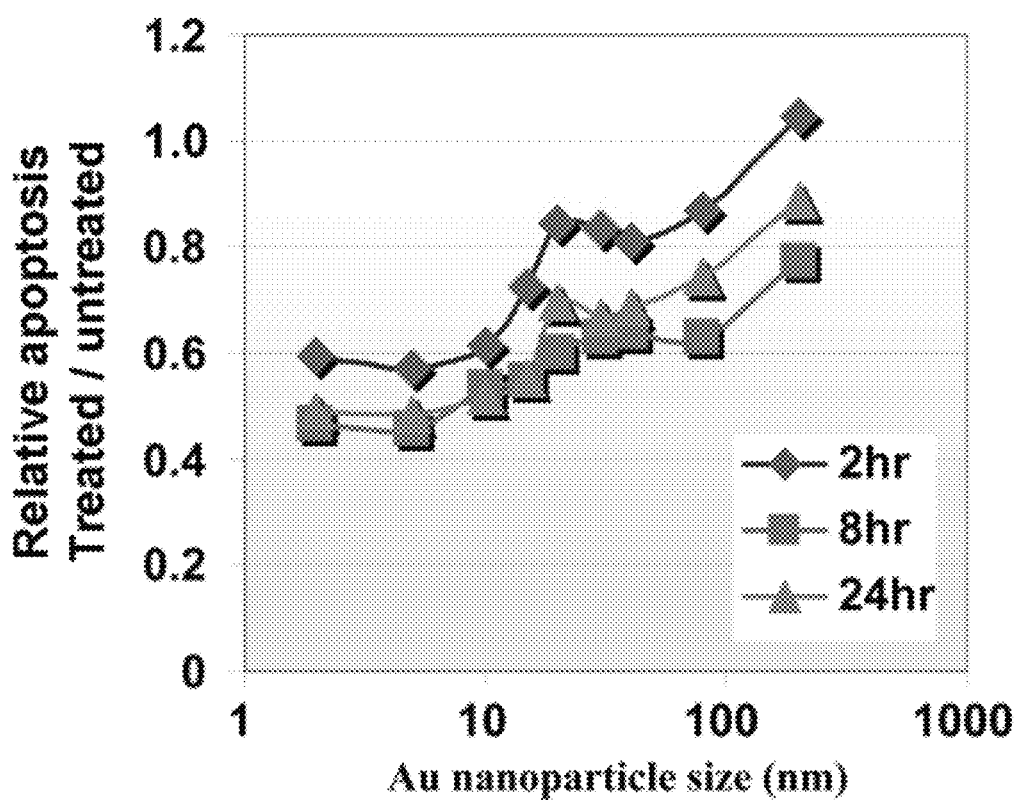
FIG. 10. Au nanoparticles ranging from 2 to 200 nm are used to treat a model cell system (Jurkat cells) at 1.2 mg/L final concentration. Less than 1.2% of total cells show apoptosis. Result shows no significant difference from untreated cells, which have an apoptosis rate of 1%. The results show absence of toxicity with Au nanoparticles in the same size range.

The highly stable, thin (10 nm) film (Au) coating provides biocompatibility, as demonstrated by experimental results (FIG. 10). Furthermore, the Au thin film deposition process can be well controlled to allow tunable absorption spectra, allowing PAT at different optical wavelengths (see FIG. 8). It has been demonstrated that a variety of gold nanocolloids are already entering in vivo clinical trials (Wang et al. (2004) *Nano Lett.*, 4: 1689-1692; Dun et al. (2007) *Nano Lett.*, 7: 941-945; Huff et al. (2007) *Nanomedicine-UK* 2: 125-132; Lee and El-Sayed (2006) *J. Phys. Chem. B*, 110: 19220-19225; Loo et al. (2005) *Nano Lett.*, 5: 709-711; Kim et al. (2007) *Appl. Phys. Lett.*, 90: 223901). Among them, Au nanorods present particularly good optical absorption in the near-infrared region, tunable by changing the aspect ratio. It has already been demonstrated that gold nanorod contrast agents can be imaged with PAT, both ex and in vivo (Chamberland et al. (2008) *Nanotechnology* 19: 95-101; Eghtedari et al. (2007) *Nano Lett.*, 7: 1914-1918). Our study has shown that the sensitivity of PAT in imaging the nanowonton is equivalent to that for gold nanorods. In fact, the MRI contrast is also expected to be strongly dependent on the shape of the nanoconstruct. It is envisaged that nanorods or needle-shaped structures can elicit greater contrast because of larger shape-induced susceptibility gradients. The present nanowonton shape is, to first order, a compromise between optical and magnetic responses.

Furthermore, the Au sandwich structure also allows additional tuning of absorbed wavelengths (Lu et al. (200:5) *Nano Lett.*, 5: 119-124; Liu et al. (2006) *Nat. Nanotechnol.*, 1: 47-52; Liu et al. (2007) *J. Nanosci. Nanotechnol.*, 7: 2323-2330). This can further improve the sensitivity of the PAT technique. Last, the Au coatings are especially attractive because of the possibility of conjugating the particles with specific molecules such as antibodies, specific ligands, thiol functional groups and therapeutic drugs, opening up prospects for targeted molecular imaging (Wickline and Lanza (2002) *J. Cell Biochem.*, 90-97). An additional imaging modality built into our nanoconstruct is the optical thermal conversion capability making these structures highly suited for photothermal therapy (Loo et al. (2005) *Nano Lett.*, 5: 709-711; Liu et al. (2006) *Nat. Mater.*, 5: 27-32; Loo et al. (2004) *Technol Cancer Res.*, T 3: 33-40; Chou et al. (2005) *J. Phys. Chem. B*, 109: 11135-11138; Hirsch et al. (2003) *Proc. Natl. Acad. Sci., USA*, 100: 13549-13554).

Methods

Fabrication of the Nanowontons.

A schematic diagram of the fabrication procedure is illustrated in FIG. 1. First, a batch-fabricated vertical silicon nanopillar array was fabricated on the surface of a 4-inch diameter silicon wafer. The coverage of the nanopillar structure was ~90% of the total wafer surface area.

On the top of each silicon nanopillar, there was a spherical silicon oxide nanostructure.

Four metallic layers of 5-nm chromium, 10-nm gold, 10-nm cobalt, and 10-nm gold were sequentially deposited on the wafer surface. However, after deposition, the sidewalls of all of the nanopillars remained exposed. The silicon wafer was therefore immersed in a 10% KOH bath solution at 80° C., aching away the nanopillars from the unprotected sidewalls in 10 min, The multilayer metallic nanostructure on the top of the nanopillars was lifted off and suspended in the KOH bath solution. Because silicon oxide and chromium were also etched away by KOH, only the gold-cobalt-gold sandwich nanostructures, the nanowontons, remained in solution. These were finally separated by centrifugation. The SEM, TEM, and size distribution measurements are shown in FIG. 2 A-C. After fabrication, these samples were chemically analyzed by inductively coupled plasma mass spectrometry (ICP-MS), measuring the total amount of Co or Au ions. By assuming bulk parameters of the materials and the size of the nanoparticles, we deduced the mass of Co and Au per nanoparticle, and calculated the nanoparticle concentration.

PAT System.

Figure 6:
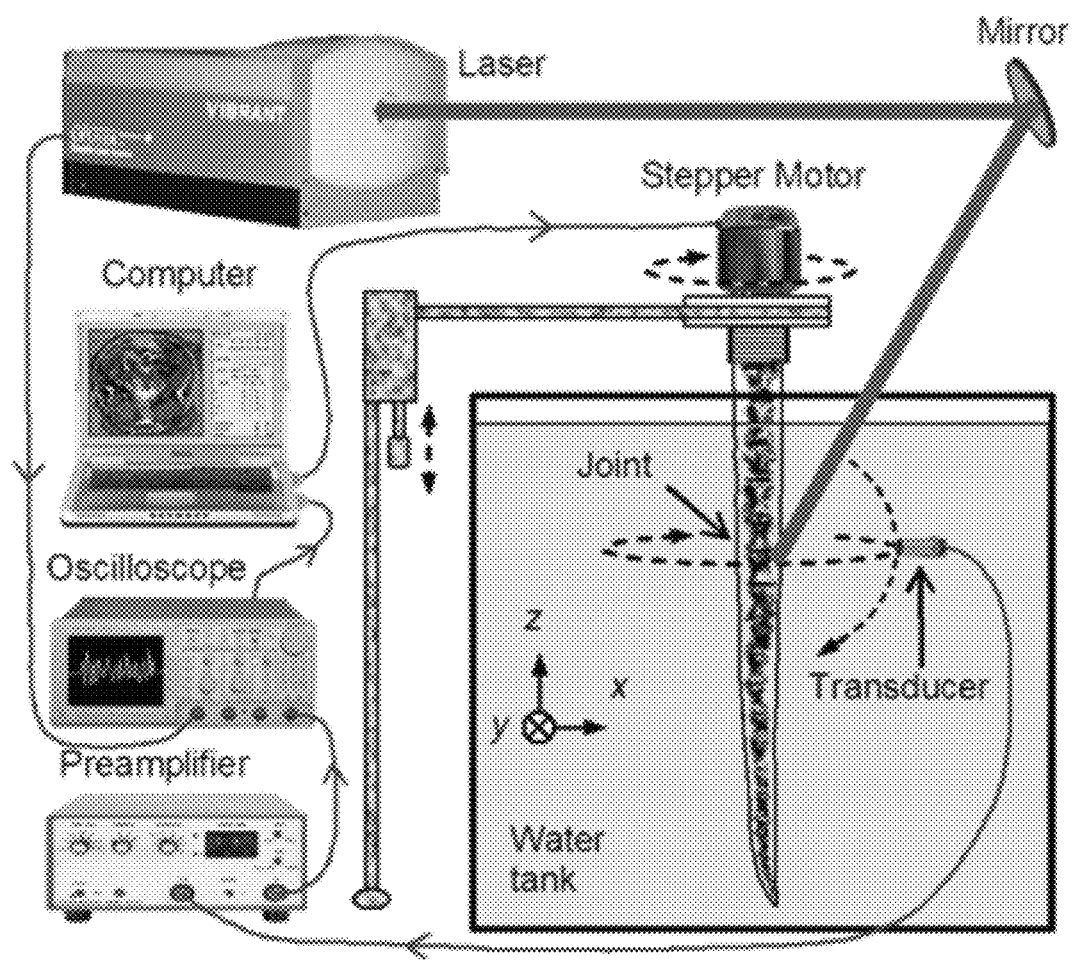
FIG. 6 illustrates a schematic of PAT (photoacoustic tomography) system in accordance with one embodiment of the present invention.

The PAT system is schematically shown in FIG. 6. An OPO (Vibrant B; Opotek) pumped by an Nd/YAG laser (Brilliant B; Bigsky) was used to provide laser pulses with a repetition rate of 10 Hz and a pulse width of 5 ns. In this study, the wavelength of the laser light was tuned to 700 nm, which was in the near-infrared region and enabled good penetration in biological tissues. The laser beam, after being expanded and homogenized, illuminated the imaged sample with an input energy density of ~10 well below the American National Standards Institute safety limit of 22 mJ/cm$^2$ at the applied wavelength.

The laser light penetrated into the sample and generated photoacoustic signals that were scanned by an ultrasonic transducer (XMS-310; Panametrics) with a center frequency at 10 MHz and a receiving bandwidth of 100%. To realize 2D cross-sectional imaging, the sample was rotated axially in the xy plane while the transducer and the laser beam were kept static. To couple the signals, the sample and the transducer were immersed in water. After a preamplifier (PR5072; Panametrics), the detected signals were digitized by an oscilloscope (TDS 540B; Tektronics) and then collected by a computer. The current PAT system exhibits spatial resolution of 200 μm in the xy plane, which has been verified by measuring the line spread function (LSF) (Chou et al. (2005) *J. Phys. Chem. B.* 109: 11135-11138).

Photoacoustic Imaging on Phantoms.

To demonstrate the PAT imaging contrast, we constructed a phantom made of 5% porcine gel in which 4 inclusions with different concentrations of nanowontons are embedded (FIG. 3). Cylindrical shaped phantoms with a 20-mm diameter were made from porcine gel. Spherical-shaped droplets with a size of 2.8 mm were made with the same gel and contained different concentrations of the contrast agent. These droplets were embedded 1 cm deep in the phantoms. For example, the phantom shown in FIG. 3 contains 4 such embedded droplets, where the nanowonton concentrations were 100, 50, 25, and 13 pM. The corresponding PAT image is shown in FIG. 3A, the locations of the objects being marked with dashed circles. In FIG. 3A, we have also quantified the contrast-to-noise ratio (CNR)=$(S_o/S_b)/\sigma$, where $S_o$ is the average intensity within the object, $S_b$ is the average intensity within the background defined by the mean of all of the pixels in the image beyond the big dashed circle (i.e., the area out of the gel phantom), and σ is the standard deviation. The computed CNRs for the objects A, B, C, and D are 10.6, 5.7, 2.1, and 1.0. It is clear that the objects A, B, and C have been imaged with sufficient optical absorption contrast.

MRI of the Phantoms.

For the phantom MRI studies, 6 holes were drilled into a (~3 cm diameter) Teflon cylinder, azimuthally distributed around the center. The phantom is shown in FIGS. 4A-4D. Each hole was 5 mm in diameter and ~1 cm deep. Two similar pieces (A and B) were machined. Nanocalloidal solutions of the nanowonton in (5%) agarose gel were prepared in concentrations of 500, 375, 250, 125, 50, 12.5, 5, and 2.5 pM. The agarose gel was heated until it became transparent, and the nanoparticles were subsequently transferred to the hot agarose, preparing the desired concentrations. Precise volumes of the nanocolloids were then slowly transferred to the cylindrical recesses and allowed to cool in ambient conditions, ensuring that no air bubbles were formed during the cooling. The solutions were intermittently pried to ensure that the distribution of the nanowontons would be kept as uniform as possible. The tops and bottoms of the phantoms were sealed with polystyrene to prevent leakage during phantom handling. The phantom A contained the concentrations 500, 375, 250, 125, and 50 pM, whereas B contained 125, 12.5, 5, and 2.5 pM. The latter had 1 cylinder empty, and each of the phantoms was also loaded with 0.6 mM $MnCl_2$ doped water to act as the control reference.

The MRI was performed in a 300-MHz NMR spectrometer (Varian Inova) equipped with triple-axis magnetic field gradients. The phantoms were imaged by using a spin-echo pulse sequence, with slice selection along the z axis, phase encoding along the y axis, and readout along the x axis. We used an echotime (TE) of 50 ms and recycle time (TR) of 1 s. The field of view was 3×3 cm, the number of points was 256×128, and the slice thickness along the z direction was 1 mm. $T_2$ measurements were also performed by repeating the spin echo sequence with varying TEs; the values used were 10, 30, 40, 50, 100, 150, and 200 ms.

MRI on Mouse Muscle.

For the animal studies, the mouse was i.p. anesthetized with 400 μL of Avertin. After 5 min, 50 μL of 60-nm-sized gold-coated Co nanoparticles at 50 pM in a solution of PBS were intramuscularly injected into the leg. As a control, PBS solution without the nanoparticles was also injected in the diametrically opposite position to the site of injection of the cobalt nanowonton. After an additional 10 min, the mouse was killed and placed into the vertical bore of the Varian 300-MHz NMR spectrometer. The mouse tail was then imaged by using a $T_2$-weighted spin-echo sequence. Multiple transverse slices were imaged, the slice thickness (along the z direction) being 0.5 mm, the TR was 1 s, the number of points was 256×128, and the field of view was 2.6×2.6 cm.

Supporting Materials.

MRI Contrast Sensitivity.

It is instructive to examine possible reasons for the superior MRI contrast enhancement. Larger (micron-size) superparamagnetic particles can be manufactured by embedding nanoparticles into a polymer matrix. It is unclear; however, that the net moment would be expected to increase linearly with the size of the construct as due to the misalignment of the multiple magnetic domains, some amount of cancellation will take place, leading to a smaller net magnetic moment per unit volume and also per particle. This is true even in the presence of a strong magnetic field as used in MRI, because the anisotropy energy of the material which causes the random reorientation of single domains is typically much larger than the Zeeman energy. When comparing our Co nanowonton to conventional small paramagnetic iron oxide (SPIO) particles under an applied field that saturates the magnetization (including any hysteresis effect), the relevant quantity for molecular imaging purposes, where a binding event involves one ligand moiety per target molecule, is the per-particle retaxivity. In a homogeneous solution of ferromagnetic particles, the per-particle relaxivity for water is proportional to the square of the magnetic moment of relaxing centers. The saturation magnetization of fcc-Co is 3.42 times higher than magnetite ($Fe_3O_4$) (Hutten et al. (2004) *J. Biotechnol.*, (12:

47-63), which implies a per-particle relaxivity that is nearly 12 times larger than magnetite. This has important implications for $T_2$-weighted MRI, which depends exponentially on the relaxation rate. For example, a 1 µM concentration of Co nanowonton particles with $T_2$ relaxivity of $1\times10^7$ s$^{-1}$ mM$^{-1}$ (as measured experimentally for our nanowonton) and an echo time of 50 ms produces an exponential decay factor that is 100 times larger than for magnetite. This is how substantial improvements in NMR signal changes can be obtained for the same particle size. Regarding our actual numbers, the measured $T_2$ relaxivity is $1\times10^7$ s$^{-1}$ mM$^{-1}$, which is a 5-orders-of-magnitude higher "per-particle" relaxivity than the monocrystalline iron oxide nanoparticles (MION) of Lu et al. (2006) *Nanotechnology* 17: 5812-5820, in which a rather low 121 ms$^{-1}$ M$^{-1}$ was obtained. Our particles are also bigger than Lu's (Id.) (60 nm average diameter, vs. 18 nm). This larger particle diameter adds a factor of 37 to the magnetic moment per particle, or 3 orders of magnitude to the relaxivity. These two effects (choice of material, particle diameter) add up to 5 orders of magnitude, which explain the difference between our results and Lu's results on iron oxide (Id.). In FIG. 9 of Lu's paper, we can see that they require $10^{-4}$ M concentrations to observe an effect in the $T_2$-weighted contrast in phantoms. Our particles can be readily seen at $2.5\times10^{-12}$ M in MRI images. This is a >7 orders of magnitude difference; this number includes the exponential effects of $T_2$-weighted contrast mentioned above. Cho et al. (2006) *Nanotechnology* 17: 640-644, report better results on Fe/Au nanoparticles, as would be expected for iron based on its high saturation magnetization, but they only report detectability thresholds of 300 pM in phantoms. (One could argue that the 300 pM cannot be seen in their FIG. 4, and the number is probably more like 600 pM. Also note that they report metal concentrations. The numbers we quote are converted to particle concentrations for comparison.) This number falls short of our cobalt nanoparticles detectability threshold. Their reported $T_2$ relaxivity, when converting the number 28.15 nM$^{-1}$ s$^{-1}$ from their Table 1 to per-particle relaxivity (using 1 mM=6 nM for iron particles of 18-nm diameter), we get ~$4\times10^6$ nM$^{-1}$ s$^{-1}$, slightly lower than ours. Because fcc-Fe has a higher saturation magnetization, there is potential for even higher particle relaxivity than cobalt by further increasing the particle diameter, but this is not demonstrated in their paper.

In Vivo Toxicity Stability

Au nanoparticles are widely used in EM studies for live cells and no observable toxicity has been detected up to nM concentrations. Of all of the metal coatings examined so far, Au coatings have shown the lowest levels of toxicity. In animal studies, Au nanoparticles such as nanoshells have shown good dose tolerance (see, Liao et al. (2006) *Nanomedicine* 1: 201-208; Cai et al. (2007) *Invest Radiol* 42: 797-806; and Kim et al. (2007) *J. Am. Chem. Soc.*, 129: 7661-7665 for relevant studies that establish the in vivo nontoxicity of Au particles). In dose-dependent studies, we have demonstrated see FIG. 8) that up to micromolar concentration, Au nanoparticles induce no elevated apoptosis in cells.

Extension to Other Modalities.

As shown in FIG. 9, there are situations where complementary information is crucial, as it is easy to find situations where single modality imaging will be insufficient. We believe that the combined PAT/MRI is extremely powerful for diagnostic imaging. MRI provides volume information whereas PAT provides edge detection. Our particles could certainly be used with position emission tomography (PET) using Au-coated radioactive cobalt, e.g., $^{60}$Co, and CT. PAT, although in relative infancy compared to PET and CT, has the exciting possibility of providing edge-detection contrast, which is a definite advantage over MRI, and other imaging modalities.

PAT Imaging of Rat Tail Joints.

CD hairless rats (~300 g; Charles River Laboratory) were included in this study. Whole tails were harvested from the rat bodies shortly after the rats were killed. An electrocautery device (SurgiStat; Valleylab) was then used to clot blood and seal vessels. Each rat tail was placed in the PAT system along the Z-axis as shown in FIG. 6. The first proximal segment of the rat tail was fixed on a rotational stage that, driven by a stepper motor, could rotate the tail around its axis. The imaged joint was about 2.5 cm from the rat trunk, where the diameter of the tail joint was 8-9 mm. First, a PAT image of a rat tail joint was taken before the administration of the contrast agent. After that, 0.05 mL of agent with a concentration of 100 pM was injected intraarticularly along the direction indicated by the arrows in FIG. 9B. Then another PAT image of the same joint was taken. The total numbers of nanowonton particles introduced into the regional joint tissue were on the order of $10^9$ (i.e., femtomole). All of the experimental parameters for the images taken before and after the administration were kept the same, except that the sample might be moved slightly during the administration of contrast agent.

Cross-sectional imaging of the rat tail joint with and without injection of the nanowonton contrast agent (0.05 ml, 100 pM) are compared in FIGS. 9A and 9B. Following the administration of contrast agent, which perfused the front part of the joint space, hyperintensities are readily observed in the periosteum (FIG. 9B). With a comparatively limited detection bandwidth, the current PAT system is more sensitive to the edges of an absorbing object (arrow in FIG. 9 B). Although the sensitivity of this PAT system to nanowonton contrast agent can be improved further by employing a laser source with better energy stability and a more sensitive transducer(s), this level of detection sensitivity is similar to or even higher than pure optical imaging for metallic particles. The general tendency of PAT to perform edge detection is evident when high frequency ultrasound detection is used. PAT with deeper penetration depth can be achieved by using laser light in the near infrared region, capitalizing on the ability to tune the absorption profile of the nanoparticles or the thin film coatings (FIG. 7). An anatomical section of the same tail joint is presented in FIG. 9C.

Conclusion it is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A layered nanoparticle characterized by having a first concave external surface and a second convex external surface, said nanoparticle comprising:
  a first biocompatible layer comprising a first surface and a second surface, the first surface being substantially concave and forming said first concave external surface of the layered nanoparticle;
  a second biocompatible layer comprising a first surface and a second surface, the second surface being substantially convex and forming said second convex external surface of the layered nanoparticle; wherein the first biocompatible layer ranges in thickness from about 1 nanometer to about 50 nanometers, wherein the inner core material ranges in thickness from about 1 nanometer to about 100 nanometers, and wherein the second biocompatible layer ranges in thickness from about 1 nanometer to about 50 nanometers and an inner core material encapsulated between, the first and second biocompatible layers.

2. The layered nanoparticle of claim 1, wherein said inner core material comprises a material selected from the group consisting of a ferro-magnetic material, a paramagnetic material, a superparamagnetic material, a radioactive material, a pharmaceutical, and a toxin.

3. The layered nanoparticle of claim 1, wherein the inner core material comprises a non-biocompatible material.

4. The layered nanoparticle of claim 3, wherein the said inner core material comprises a radioactive material.

5. The layered nanoparticle of claim 1, wherein the inner core material comprises a ferro-magnetic material.

6. The layered nanoparticle of claim 5, wherein the inner core material comprises a ferro-magnetic material comprising a material selected from a group consisting of iron (Fe), nickel (Ni), cobalt (Co), gadolinium (Gd), an alloy thereof, a nitrate thereof, a nitrite thereof, a nitride thereof, and an oxide thereof.

7. The layered nanoparticle of claim 6, wherein the said inner core material comprises a radioactive material selected from the group consisting of $^{125}$I, $^{35}$S, $^{14}$C, $^{32}$P, $^{11}$C, $^{38}$K, $^{89}$K, $^{89}$Zr, $^{217}$Bi, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{90}$Y, $^{131}$I, $^{123}$I, $^{99}$In, $^{131}$I, $^{64}$Cu, $^{68}$Ga, and $^{111}$Ag.

8. The layered nanoparticle of claim 1, wherein the first biocompatible layer comprises a material selected from the a group consisting of gold, aluminum, titanium, niobium, tantalum, nickel, ruthenium, rhodium, palladium, silver, osmium, iridium, platinum, nitenol, a cobalt base alloy, an alloy thereof, a nitrate thereof, a nitrite thereof, a nitride thereof, and an oxide thereof.

9. The layered nanoparticle of claim 8, wherein the first biocompatible layer and the second biocompatible layer comprise the same material.

10. The layered nanoparticle of claim 1, wherein the first biocompatible layer and the second biocompatible layer comprise different materials.

11. The layered nanoparticle of claim 1, wherein the layered nanoparticle is configured to absorb radiation over a range selected from a group consisting of infrared wavelength, visible light wavelength, ultraviolet wavelength, microwave wavelength, and x-ray wavelength.

12. The layered nanoparticle of claim 1, wherein the first biocompatible layer comprises gold, wherein the inner core material comprises cobalt, and wherein the second biocompatible layer comprises gold.

13. The layered nanoparticle of claim 1, wherein a longest dimension of the layered nanoparticle is less than or equal to about 500 nanometers.

14. The layered nanoparticle of claim 1, wherein the layered nanoparticle is attached to a moiety selected from a group consisting of a protein, an antibody, a lectin, and a nucleic acid.

15. The layered nanoparticle of claim 1, wherein said the second biocompatible layer comprises a material selected from the a group consisting of gold, aluminum, titanium, niobium, tantalum, nickel, ruthenium, rhodium, palladium, silver, osmium, iridium, platinum, nitenol, and a cobalt base alloy, an alloy thereof, a nitrate thereof, a nitrite thereof, a nitride thereof, and an oxide thereof.

16. The layered nanoparticle of claim 15, wherein the first biocompatible layer and the second biocompatible layer comprise the same material.

17. The layered nanoparticle of claim 1, wherein said nanoparticle is configured to absorb radiation at a near-infrared wavelength.

18. The layered nanoparticle of claim 1, wherein said nanoparticle is configured to absorb radiation at a wavelength of about 700 nm.

\* \* \* \* \*